(12) United States Patent
Burbank et al.

(10) Patent No.: US 10,525,190 B2
(45) Date of Patent: Jan. 7, 2020

(54) MEDICAL DEVICE LEAK SENSING DEVICES, METHODS AND SYSTEMS

(71) Applicant: NXSTAGE MEDICAL, INC., Lawrence, MA (US)

(72) Inventors: Jeffrey H. Burbank, Boxford, MA (US); Dennis M. Treu, Castle Rock, CO (US); James M. Brugger, Newburyport, MA (US); Daniel Joseph Rubery, Jr., Windham, NH (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 194 days.

(21) Appl. No.: 15/655,091

(22) Filed: Jul. 20, 2017

(65) Prior Publication Data
US 2017/0312419 A1    Nov. 2, 2017

Related U.S. Application Data

(62) Division of application No. 14/238,434, filed as application No. PCT/US2012/050965 on Aug. 15, 2012, now Pat. No. 9,724,459.

(60) Provisional application No. 61/523,752, filed on Aug. 15, 2011.

(51) Int. Cl.
*A61M 1/36* (2006.01)
*G01M 3/04* (2006.01)

(52) U.S. Cl.
CPC .......... *A61M 1/3656* (2014.02); *A61M 1/367* (2013.01); *G01M 3/04* (2013.01); *A61M 2205/15* (2013.01); *Y10T 137/5762* (2015.04)

(58) Field of Classification Search
None
See application file for complete search history.

(56) References Cited

U.S. PATENT DOCUMENTS

| | | | |
|---|---|---|---|
| 4,479,760 A | 10/1984 | Bilstad et al. | |
| 4,617,115 A | 10/1986 | Vantard | |
| 5,674,390 A | 10/1997 | Matthews et al. | |
| 5,725,773 A | 3/1998 | Polaschegg | |
| 5,919,369 A | 7/1999 | Ash | |
| 6,221,040 B1 | 4/2001 | Kleinekofort | |
| 6,471,855 B1 | 10/2002 | Odak et al. | |
| 6,572,576 B2 | 6/2003 | Brugger et al. | |
| 7,040,142 B2 | 5/2006 | Burbank | |

(Continued)

OTHER PUBLICATIONS

International Search Report and Written Opinion for International Application No. PCT/US12/50965, dated Jan. 22, 2013.

*Primary Examiner* — Richard C Gurtowski
(74) *Attorney, Agent, or Firm* — Potomac Law Group, PLLC; Mark Catan

(57) ABSTRACT

Features for protecting against leaks in a fluid circuit are disclosed. In an embodiment, a first indicator of a leak is used to trigger confirmation by blood flow reversal and air detection in the blood circuit. A method for performing a blood treatment includes, at blood treatment machine, pumping blood to a patient through a first blood line. Further, at a controller of the blood treatment machine, a first signal is received, indicating a probability of a leak in the first blood line. Responsively to the first signal, the controller commands a leak verification operation and receives a second signal indicating whether a leak in the first blood line is verified. Further, a leak indicating signal is generated if the second signal indicates a leak is verified.

14 Claims, 14 Drawing Sheets

(56) References Cited

U.S. PATENT DOCUMENTS

| | | |
|---|---|---|
| 7,544,300 B2 | 6/2009 | Brugger et al. |
| 8,002,727 B2 | 8/2011 | Brugger et al. |
| 8,105,487 B2 | 1/2012 | Fulkerson et al. |
| 8,298,167 B2 | 10/2012 | Peters et al. |
| 2005/0020959 A1 | 1/2005 | Brugger et al. |
| 2008/0214979 A1 | 9/2008 | Brugger et al. |
| 2010/0004588 A1 | 1/2010 | Yeh et al. |
| 2011/0315611 A1 | 12/2011 | Fulkerson et al. |

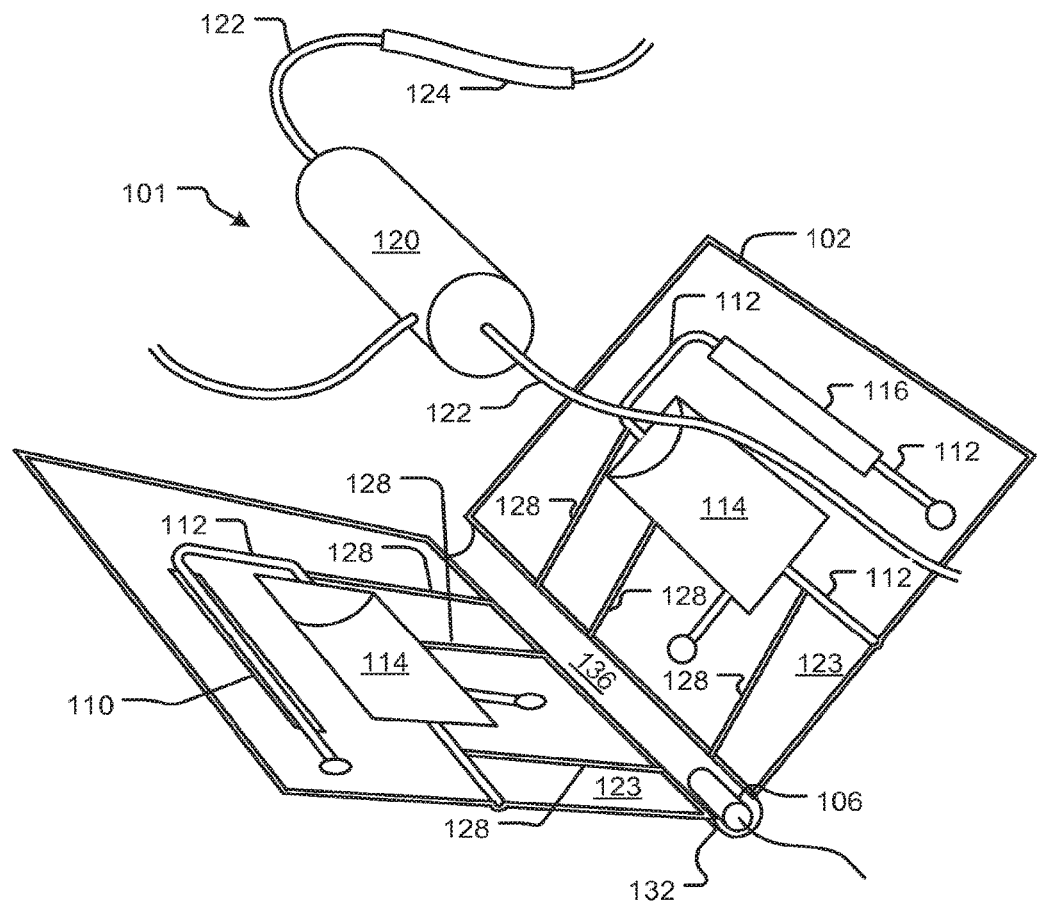
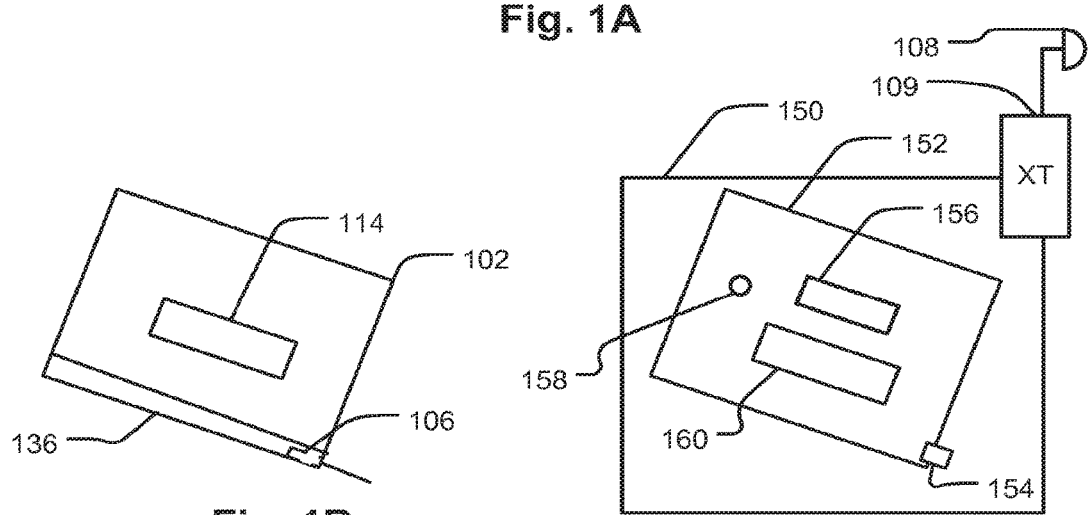
Fig. 1A
Fig. 1B
Fig. 1C

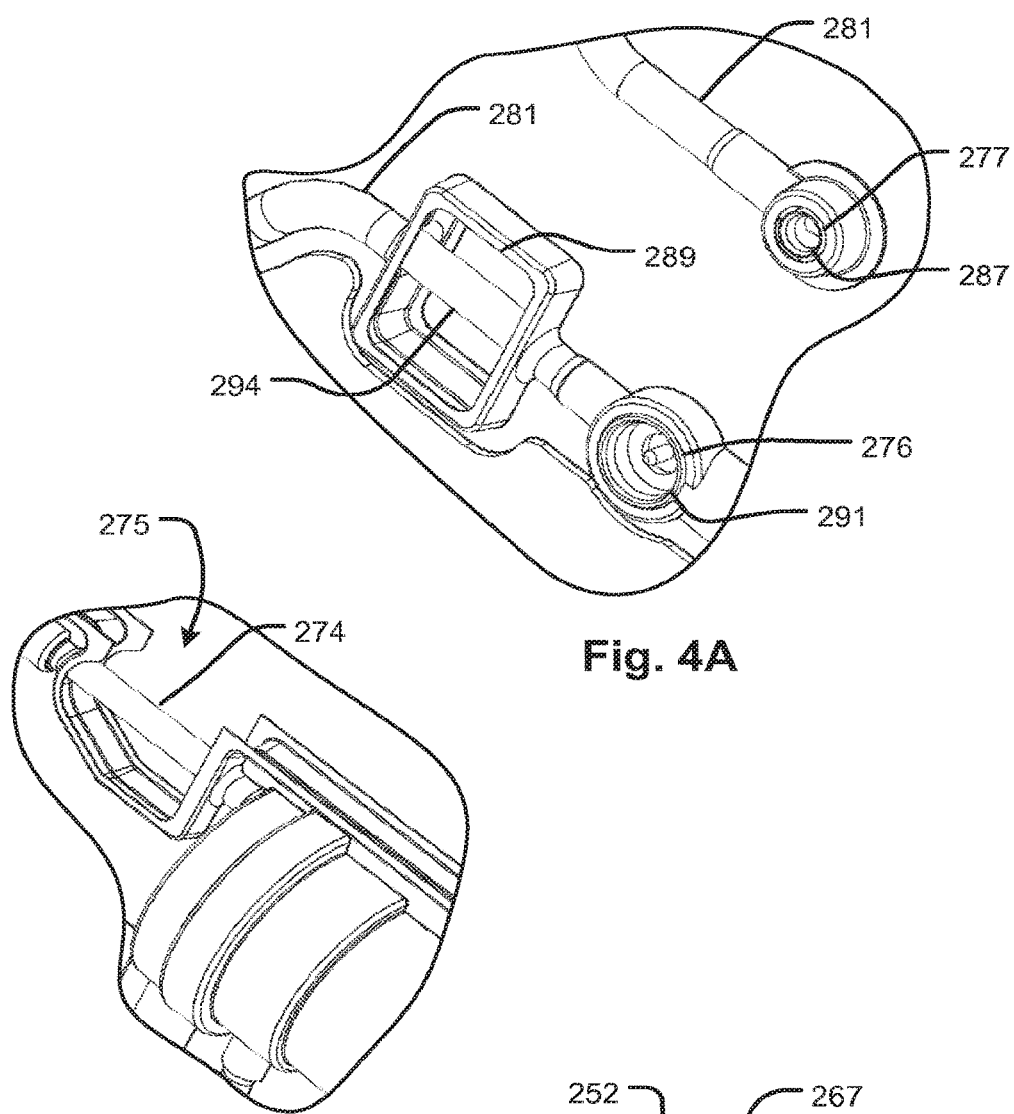
Fig. 4A
Fig. 4B
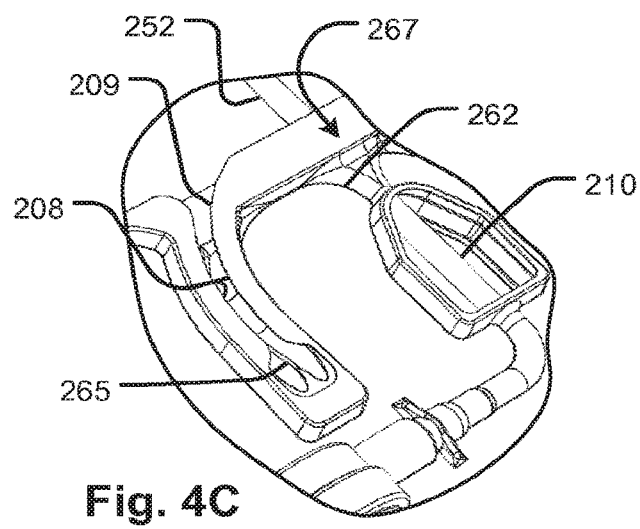
Fig. 4C

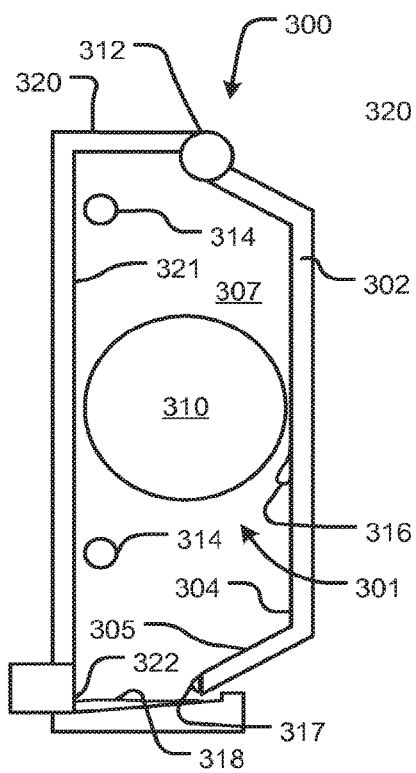
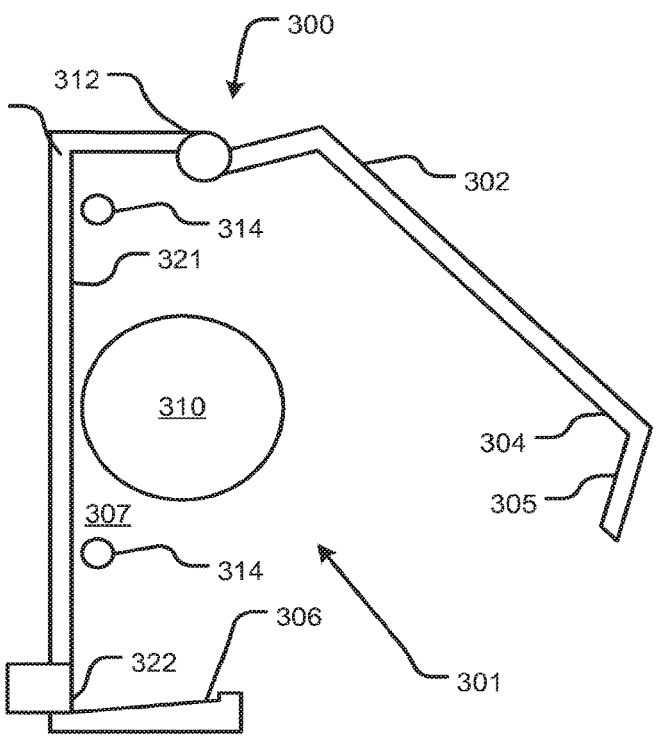
Fig. 6A  Fig. 6B
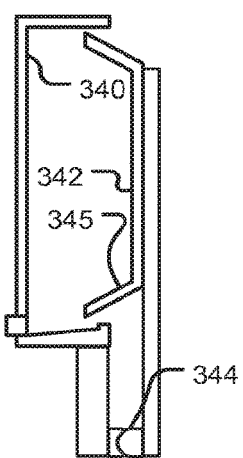
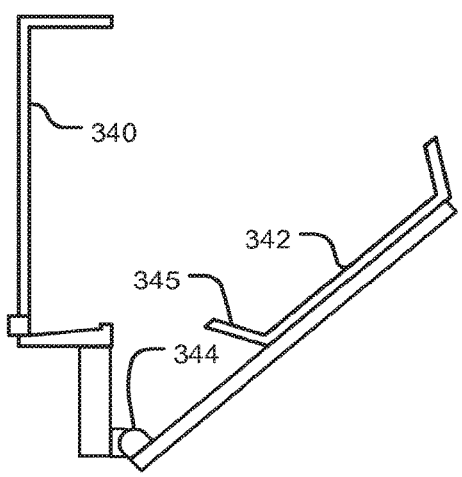
Fig. 6C  Fig. 6D

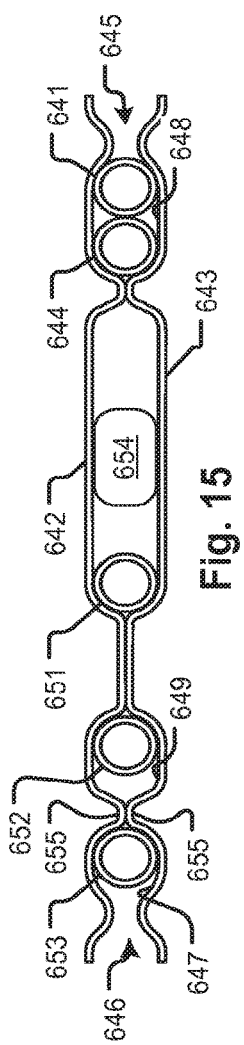
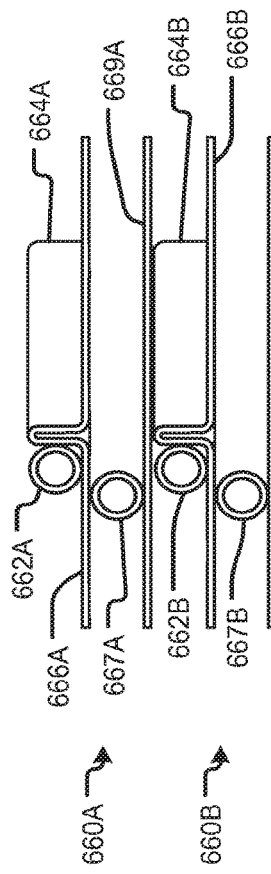
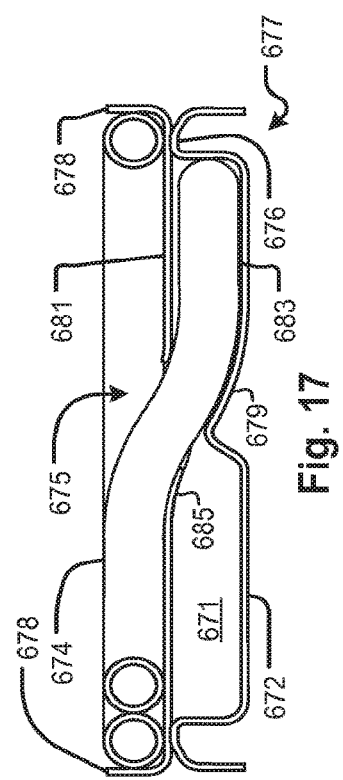
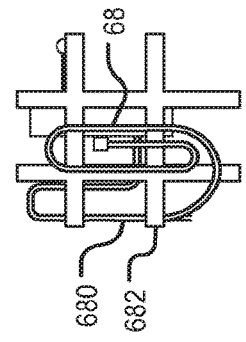

MEDICAL DEVICE LEAK SENSING DEVICES, METHODS AND SYSTEMS

CROSS REFERENCE TO RELATED APPLICATIONS

The present application is a divisional of U.S. patent application Ser. No. 14/238,434, filed Jul. 18, 2014, which is a national stage entry of International Application No. PCT/US12/50965, filed Aug. 15, 2012, which claims the benefit of U.S. Provisional Application No. 61/523,752, entitled MEDICAL DEVICE LEAK SENSING DEVICES, METHODS, AND SYSTEMS, filed Aug. 15, 2011, the entirety of all of which is hereby incorporated by reference herein.

FIELD

The present invention relates to the detection of leaks in fluid circuits and to devices for supporting fluid circuit components and for connecting the same to treatment machines.

BACKGROUND

Many medical procedures involve the extraction and replacement of flowing blood or other biological fluid such as plasma from, and back into, a donor or patient. When the fluid is outside the patient it is conducted through machinery that processes the fluid. Examples of treatment processes include, but are not limited to, hemodialysis, hemofiltration, hemodiafiltration, blood and blood component collection, plasmapheresis, apheresis, and blood oxygenation.

The processes listed above, and others, may involve the movement of large amounts of fluid at a very high rate. For example, 500 ml of blood may be drawn out and replaced every minute, which is about 5% of the patient's entire supply. If a leak occurs in such a system, the patient could be drained of enough blood in a few minutes to cause loss of consciousness and even death. The lost blood and other fluids may pose other risks including economic and health risks. As a result, extracorporeal fluid circuits are normally used in very safe environments, such as hospitals and treatment centers, and attended by highly trained technicians and doctors nearby. Even with close supervision, a number of deaths occur in the United States every year due to undue blood loss from leaks.

Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies.

Approaches for detecting leaks are described, for example in U.S. Pat. No. 5,674,390, which employs fluid detectors outside the fluid circuit to detect the presence of fluid after it has leaked. Another system that employs leak detectors external to a blood circuit is U.S. Pat. No. 7,040,142. U.S. Pat. No. 6,572,576 and U.S. Patent Publication No. 2008-0214979 (which was issued as U.S. Pat. No. 8,002,727 on Aug. 23, 2011) describe methods of detecting leaks in which flow is reversed to draw air into a positive pressure part of a leaking blood circuit (e.g., venous lines returning blood to the patient) so that air can be detected and the leak identified automatically.

Yet another method for detecting a leak in a fluid circuit, for example a vascular access, is to monitor the pressures in the arterial and venous lines and compare their levels and changes therein to leak profiles, thereby permitting machine detection of a leak. An example of such a system is described in U.S. Pat. No. 6,221,040. The former four U.S. patents and one patent Publication, identified immediately above are hereby incorporated by reference in their entireties herein. In the provisional phase of this application, the above four patents and patent publication were attached as Appendices I, II, III, IV, and V.

Leak safe systems have also been proposed which rely on the detection of leaks by detecting fluid outside an expected flow path. For example, a resistance between two spaced dry electrodes may drop precipitously when wetted by blood or other fluid. The change in resistance may be detected by a galvanometer and used to generate an alarm signal.

There is a continuing need in the art for ultra-safe systems that can be used in a non-clinical setting and/or without the need for highly trained and expensive staff. Reliable mechanisms to preventing and detecting leaks of blood and other fluids are desirable. The detection of leaks involves a trade-off between sensitivity and the frequency of false detection. If a system is overly sensitive, there is a high risk of many false alarms, which can lead to operator "alarm fatigue" which can cause operators to cancel alarms without duly investigating the cause. Such a response to alarm fatigue can subvert the function of sensitive leak detection.

SUMMARY

The disclosed subject matter employs two mechanisms for blood leak detection which may be combined in a single system with multiple other mechanisms. In a first mechanism, a blood circuit is enclosed in a closely conforming enclosure that prevents fluid from escaping without requiring a fluid-tight seal and conducts any leaking fluid to an external leak detector. The enclosure provides convenient access for loading and can accept fluid circuits encased within cartridges and bare fluid circuits. In a second mechanism, a leak is preliminarily detected using one or more highly sensitive detection devices, such as a time rate of change of pressure in a blood line. A preliminary leak detection signal is used to trigger a reversal of the flow of fluid, which creates a negative pressure in the normally positive pressure line, which forces air to be drawn into the line if a leak is actually present. If air is drawn in, then a leak is indicated by a corresponding output.

Embodiments of the disclosed subject matter include a packaged fluid circuit for a blood treatment system with a treatment cartridge-type support having a folding clamshell configuration defining internal recesses that at least partly enclose portions of a fluid circuit, the fluid circuit having tubing portions and connector portions. The tubing portions have extending sections that extend outside the support, emerging from tubing openings in a cartridge. The cartridge defines a horn-shaped one of the openings in the cartridge that is formed by bringing two halves of a foldable sheet together, the horn-shaped opening progressively narrowing to a cylindrical recess defined between concave recesses in each half of opposing portions of the foldable sheet. The extending sections being coiled in a loop with a restraint to retain the coil and hold it on the support such that the tubes extend through the horn shaped ports in an arc into the coil without kinking.

In other embodiments, a packaged fluid circuit for a blood treatment system includes a treatment cartridge-type support having a folding clamshell configuration defining internal recesses that at least partly enclose portions of a fluid circuit, the fluid circuit having tubing portions and connector portions. The folding clamshell structure has a living hinge portion where facing panels of the support meet. The hinge portion has a leak sensor positioned at approximately a lower portion of the support such that leaks arising from portions of the fluid circuit lying between the panels is conveyed toward the hinge portion and therealong to the leak sensor.

Embodiments of the disclosed subject matter include a system that reverses the flow of blood in an extracorporeal treatment system in response to a pressure signal. A change in pressure of an arterial line is detected by a pressure sensor located to detect pressure of blood being conveyed in a positive pressure line. A temporal pressure profile may be acquired which shows a time-variation in pressure in the line. This profile may be stored digitally as a time series of pressure level samples according to various known techniques, for example using a strain gage type pressure sensor (e.g., drip chamber, chamberless sensors, pod-type pressure sensors using diaphragm isolators, etc.) and an analog-to-digital converter, along with appropriate processor, memory, and non-volatile or volatile data storage. The profile may be compared to a template stored in memory at regular intervals by feature matching such as correlation. In such embodiments, a drop below a threshold in the correlation coefficient of the template relative to an instant profile segment may be used to indicate a loss of normal pressurization associated with normal operation and thereafter signal an alarm. In an embodiment, the pressure change may be a result of a leak (sudden drop of pressure) or a sudden change in position of the patient or movement of the arterial line and is used to trigger a reversal of the blood flow in the positive pressure line to test for the inspiration of air into the line using air bubble detectors which are well known in the art. Thus, in the event of an indication of an abnormal pressure profile or condition, the blood flow is reversed in accord with the method and system described in U.S. Pat. Nos. 6,572,576 and 8,002,727. If a leak is not detected, an alarm may not be generated even though the pressure detection alone indicated it. Alternatively, the alarm level may be lower since there was a failure of both methods to detect the leak.

A feature of the two step system is that the use of a first level detection, such as pressure change in the blood lines, which does not require reversal, is used to trigger what may be a more disruptive test, or confirmation, namely the reversal of flow of blood. In this way reversals may occur less often than in the prior art systems. Also, false positives may occur less often than in the prior art system that relies on pressure measurement. Other devices for recognizing the pressure loss in blood lines may be employed in combination with the above or alone in various types of systems.

According to embodiments of the disclosed subject matter, a fluid handling device for a medical treatment system may have a first fluid circuit configured to process and convey fluid including at least one actuator portion and at least one sensor portion. A second fluid circuit encases the first fluid circuit and is arranged to convey fluid leaking from the first fluid circuit to a leak detection portion thereof. The leak detection portion contains a leak sensor or is configured to engage with a leak sensor. The first and second fluid circuits may be parts of a disposable component configured for use with a predefined medical treatment device. The first fluid circuit may have tube portions and the second fluid circuit may have tube-shaped channels that surround the portions first fluid circuit tube portions. The second fluid circuit may have windows that expose respective ones of the at least one actuator portion and the at least sensor portion. Each of the windows may have an extension at a lower end thereof configured to capture leaking fluid dripping from a respective one of the at least one actuator portion and at least one sensor portion. The second fluid circuit may have a curved tubing management recess configured to receive and support tubular extensions from the first fluid circuit. The first fluid circuit may include a medical treatment component. The second fluid circuit leak detection portion may be transparent. The first fluid circuit may include a dialyzer filter and a blood circuit. The medical treatment device may be configured to perform an extracorporeal blood treatment. The first fluid circuit may include a dialyzer filter and a blood circuit. The first and second fluid circuits may form a generally planar arrangement and the first fluid circuit may include connectors exposed by respective windows. The first and second fluid circuits may form a generally planar arrangement and the first fluid circuit may include connectors exposed by respective windows and configured to connect to a dialysate fluid circuit of a dialysis machine. The first fluid circuit may include a blood treatment filter having a longitudinal axis; the second fluid circuit is configured to support the blood treatment filter at a predefined angle with respect thereto; and the predefined blood treatment device is configured to hold the second fluid circuit in a predefined orientation such that the blood treatment filter longitudinal axis is held diagonally with one end above the other. The predefined blood treatment device may be configured such that the predefined orientation places the second fluid circuit leak detection portion at a bottom of the second fluid circuit. The second fluid circuit may be configured to open as a clamshell to receive the first fluid circuit. The second fluid circuit may be closed around the first fluid circuit such that a first portion thereof fits within a recess of the other. The second fluid circuit may have interior-facing surfaces, wherein all of the interior facing surfaces are sloped such that fluid leaking from the first fluid circuit are conveyed to the leak detection portion.

According to embodiments of the disclosed subject matter, a fluid handling system for a medical treatment system has a treatment device having at least one actuator and at least one sensor. A first fluid circuit is configured to process and convey fluid including at least one actuator portion and at least one sensor portion configured to engage the at least one actuator and the at least one sensor. The treatment device has a leak detector and further configured to enclose the first fluid circuit and to convey any leaks from the first fluid circuit to the leak detector. A second fluid circuit is configured to process and convey fluid including at least one actuator portion and at least one sensor portion. A third fluid circuit encases the fluid circuit and is arranged to convey fluid leaking from the first fluid circuit to a leak detection portion thereof. The leak detection portion is configured to engage the leak detector. The third fluid includes at least one actuator portion and at least one sensor portion configured to engage the at least one actuator and the at least one sensor. The second and third fluid circuits form a unitary fluid circuit device. As a result of this configuration, the treatment device is configured to detect leaks using either the unitary fluid circuit device or the first fluid circuit. The unitary fluid circuit device may be a disposable. The treatment device may include a blood treatment device.

According to embodiments of the disclosed subject matter, a method for performing a blood treatment in which a blood treatment machine pumps blood to a patient through a first blood line. A controller of the blood treatment machine receives a first signal indicating a probability of a leak in the first blood line. The controller, responsively to the first signal, commands a leak verification operation and receiving a second signal indicating whether a leak in the first blood line is verified. The controller generates a leak indicating signal if the second signal indicates a leak is verified. The controller may be configured to control a rate and direction of the pumping and the leak verification operation may include reversing a flow of blood in the first blood line and detecting air in the first blood line. The method may include generating the first signal, wherein the generating the first signal may include detecting a change of pressure in the first blood line. The method may include generating the first signal, wherein the generating the first signal may include detecting a rate of change of pressure in the first blood line. The method may also include generating the first signal, wherein the generating the first signal may include detecting a characteristic of a pressure versus time signal characterizing a flow in the first blood line.

According to embodiments of the disclosed subject matter, a system for performing a blood treatment can include a blood treatment component with a controller configured to pump blood to a patient through a first blood line. The controller is configured to receive a first signal indicating a probability of a leak in the first blood line. The controller is configured to, responsively to the first signal, command a leak verification operation and receiving a second signal indicating whether a leak in the first blood line is verified. The controller is configured to generate a leak-indicating signal responsively the second signal. The controller may be configured to control a rate and direction of the pumping and the leak verification operation may include reversing a flow of blood in the first blood line and detecting air in the first blood line. The controller may be configured to generate the first signal responsively to a detection of a change of pressure in the first blood line. The controller may be configured to generate the first signal responsively to a detection of a rate of change of pressure in the first blood line. The controller may be configured to generate the first signal responsively to a detection of a characteristic of a pressure versus time signal characterizing a flow in the first blood line.

According to embodiments of the disclosed subject matter, a blood treatment apparatus includes a blood treatment component configured to pump blood from an arterial blood line to a venous blood line. A leak sensor is configured to detect a leak with a probability of less than unity in the venous blood line. An air detector is configured to detect infiltration of air into the venous blood line. A blood flow reversing device is controlled by a controller. The controller receives a signal from the sensor and configured to reverse flow responsively to a signal from the leak sensor such that air infiltrating the venous blood line is detected by the air detector. The leak sensor may include a pressure sensor configured to detect pressure changes in the venous blood line. The leak sensor may include a data store configured to record a time series of pressure samples representing pressure in the venous blood line and a processor configured to determine a magnitude of a change in pressure within a predefined time interval. The leak sensor may include a data store configured to record a time series of pressure samples representing pressure in the venous blood line and a processor configured to determine a magnitude of a change in pressure within a predefined time interval and to indicate a leak when a rate of change in pressure exceeds a predefined range.

According to embodiments of the disclosed subject matter, a fluid circuit device can include a support and at least one tubular element. The support can have an interior space and can be generally planar in configuration with a perimeter. The at least one tubular element can have a first portion encased within the interior space and a second portion extending through an opening of the support to an outside of said interior space. The opening can have a curved guide shaped to prevent the second portion from kinking when the second portion is drawn tightly to at least one side of an axis of the opening. More than one of the openings can be provided. The second portion can be coiled in a flat loop adjacent the support and within the perimeter. The opening can face at least partly in a direction perpendicular to a major planar surface of the support. The curved guide can curve so that one end of the support is more parallel to a major planar surface of the support than another end of the curved guide such that the second portion is lifted away from the interior space. The curved guide can curve in a plane that is parallel to a major planar surface of the support. The second portion can extends toward the perimeter and can curve along and then inwardly from the perimeter back into a portion of the interior space that has a hold down member which confines the second portion within the interior space and defines a gap through which the second portion can be pulled out of confinement in the interior space in a direction perpendicular to the major planar surface so as to permit the second portion to extend directly away from the opening along the axis thereof. Alternatively, the second portion can extend toward the perimeter and can curve along and then inwardly from the perimeter back into a portion of the interior space that has a hold down member which confines the second portion within the interior space and defines a gap through which the second portion can be pulled out of confinement in the interior space in a direction parallel to the major planar surface so as to permit the second portion to extend directly away from the opening along the axis thereof. The support can be of two panels whose surfaces each define a single valued function such that it can molded and released from a vacuum mold.

In embodiments of the disclosed subject matter, a fluid circuit device can include a support and at least one tubular element. The support can have an interior space and can be generally planar in configuration with a perimeter. The at least one tubular element can have a first portion encased within the interior space and a second portion extendable through an opening of the support to an outside of said interior space. The support can have guides that releasably hold the second portion within the perimeter and at least one curved guide shaped to prevent kinking of or damage to the second portion when so held within the perimeter. The guides can be arranged and positioned to permit the second portion to be coiled in a flat loop within the perimeter. The support can be of two panels whose surfaces each define a single valued function such that it can molded and released from a vacuum mold. The support can have a partially sealed volume and can be sealed around the perimeter with openings for the second portion and to provide access to sensor and actuator portions of the circuit. The support can have a continuous fluid-tight seal along the perimeter can be configured for mounting to a predefined device in a particular orientation such that the opening is located in an upper half of said support. The support can be configured for mounting to the predefined device in a particular orientation such that the opening is located adjacent a top of said support.

In embodiments of the disclosed subject matter, a method for performing a blood treatment can include, at a blood treatment machine, pumping blood to a patient through a first blood line, and, at a controller of said blood treatment machine, receiving a pressure signal indicating a loss of pressure in said first blood line. The method can further include, at the controller, responsively to the first signal, commanding a leak verification operation, receiving a second signal indicating whether a leak in the first blood line is verified responsively to the leak verification operation, and generating a leak indicating signal if the second signal indicates a leak is verified. The controller can be configured to control a rate and direction of the pumping and the leak verification operation can include reversing a flow of blood in the first blood line and detecting air in the first blood line. The method can further include generating the first signal. The generating the first signal can include detecting a change of pressure in the first blood line.

In embodiments of the disclosed subject matter, a method for performing a blood treatment can include, at blood treatment machine, pumping blood to a patient through a first blood line, and, at a controller of the blood treatment machine, receiving a first signal of a first classifier of a leak. The method can further include, at the controller, responsively to the first signal, commanding a leak verification operation, receiving a second signal of a second classifier indicating the presence of a leak, which second signal is responsive to the leak verification operation, and generating a leak indicating signal responsively to the second signal. The leak verification operation can include halting a flow of fluid and/or reversing a flow of fluid. Alternatively or additionally, the leak verification operation can include applying a voltage or acoustic signal to a fluid and detecting the transmission or reflection responsively thereto. The second classifier can detect pressure signals indicative of patient vital signs and/or air in a fluid line and/or a current or pressure signal.

In embodiments of the disclosed subject matter, a method for performing a blood treatment can include, at blood treatment machine, pumping blood to a patient through a first blood line, and, at a controller of the blood treatment machine, receiving a first signal indicating a probability of a leak in said first blood line. The first signal can be generated responsively to a predefined change in the pressure in the first blood line and/or responsively to a calculation that is responsive to a constant pressure occurring before and after the predefined change in the pressure in the first blood line. Alternatively or additionally, the first signal can be responsive to pressure data stored in a buffer. Alternatively or additionally, the first signal can be responsive to filtered pressure data stored in a buffer, which data is filtered to remove at least one of pump noise and high pass frequency components. Alternatively or additionally, the first signal can be generated responsively to a change of 17% in the pressure in the first blood line occurring between two intervals during which the pressure remained within a predefined range for a predefined time. Alternatively or additionally, the first signal can be generated responsively to a change of a predefined magnitude in the pressure in the first blood line occurring between two intervals during which the pressure remained within a predefined range for a predefined time. Alternatively or additionally, the first signal can be generated responsively to a change of a predefined percentage of magnitude in the pressure in the first blood line occurring between two intervals during which the pressure remained within a predefined range for a predefined time. The method can further include, at the controller, responsively to the first signal, commanding a leak verification operation and receiving a second signal indicating whether a leak in the first blood line is verified. The controller can be configured to control a rate and direction of said pumping and said leak verification operation includes reversing a flow of blood in said first blood line and detecting air in said first blood line. The method can further include, at the controller, generating a leak indicating signal if the second signal indicates a leak is verified.

In embodiments of the disclosed subject matter, a method for detecting a leak in a blood flow line can include storing a time series of pressure data representing pressure in the blood flow line over time in a buffer of a controller of a blood processing device, detecting a signature in a data stored in the buffer. The signature can be adjacent intervals during which the pressure remained within a first predefined range of variation (peak to peak or variance) for a predefined time (plateau intervals), combined with a difference between a pressure representative of the two pressures during the plateau intervals exceeding a second predefined range. The second predefined range can be defined in terms of percentage magnitude change. The second predefined range can be defined in terms of absolute magnitude change.

In embodiments of the disclosed subject matter, an apparatus for performing a blood treatment can include a blood pump, sensors, actuators, a controller, and a memory. The sensors and actuators can be configured to engage with predefined blood lines including a venous line and an arterial line connectable to an access for returning blood to, and drawing blood from, a patient. The sensors can include a venous pressure sensor and an arterial pressure sensor configured to measure pressure in the venous and arterial lines, respectively. The controller can be connected to the blood pump. The memory can be in the controller and can store a procedure for storing time sequences of pressures indicated by the arterial and venous pressure sensors. The controller can be programmed to halt the blood pump responsively to a combination of both of the time sequences. The combination can include detection of a fall in pressure in the venous line that coincides with a stable pressure in the arterial line. The controller can be further configured to reverse a flow of blood responsively to the combination and thereafter, to halt the blood pump responsively to a detection of air in one of the blood lines.

In embodiments of the disclosed subject matter, an apparatus for performing a blood treatment can include a blood pump, a pressure sensor, and a control module. The blood pump can be constructed to pump blood to a patient through a first blood line. The pressure sensor can be coupled to the first blood line for measuring a pressure therein. The control module can be configured to generate a first signal indicating a probability of a leak in the first blood line responsively to a predefined change in the pressure in the first blood line as measured by the pressure sensor. The control module can be configured to generate the first signal responsively to a predefined change in the pressure in the first blood line and responsively to a calculation that is responsive to a constant pressure occurring before and after the predefined change in the pressure in the first blood line. The apparatus can also include a buffer for storing pressure data therein. The first signal can be responsive to the pressure data stored in the buffer. The control module can be configured to subject the pressure data stored in the buffer to filtering so as to remove at least one of noise from said blood pump and high-pass frequency components. Alternatively or additionally, the control module can be configured to generate the first signal responsively to a change of a predefined magnitude or percentage in the pressure in the first blood line occurring between two intervals during which the pressure remained within a predefined range for a predefined time. The apparatus can also include a second control module for controlling the blood pump. The second control module can be configured to command a leak verification operation in response to the first signal. The apparatus can further include a detector configured to detect air in the first blood line. The second control module can be configured to control a rate and direction of the blood pump. The leak verification operation can include reversing a flow of blood the in a first blood line and using the detector to detect air in the first blood line. The second control module can be configured to generate a leak indicating signal when the detector detects air in the first blood line.

In embodiments of the disclosed subject matter, a controller for a blood treatment machine can be configured to generate a first signal indicating a probability of a leak in the first blood line responsively to a predefined change in pressure in the first blood line. The blood treatment machine can have a blood pump that pumps blood to a patient through the first blood line. The controller can be configured to generate the first signal responsively to a predefined change in the pressure in the first blood line and responsively to a calculation that is responsive to a constant pressure occurring before and after the predefined change in the pressure in the first blood line. A buffer can be provided for storing pressure data therein. The first signal can be responsive to the pressure data stored in the buffer. The controller can be configured to subject the pressure data stored in the buffer to filtering so as to remove at least one of noise from said blood pump and high-pass frequency components. Alternatively or additionally, the controller can be configured to generate the first signal responsively to a change of a predefined magnitude or predefined percentage in the pressure in the first blood line occurring between two intervals during which the pressure remained within a predefined range for a predefined time. The controller can be configured to command a leak verification operation in response to said first signal. The controller can be configured to control a rate and direction of the blood pump. The leak verification operation can include reversing a flow of blood the in the first blood line and detecting air in the first blood line. The controller can be configured to generate a leak indicating signal when air is detected in the first blood line.

In embodiments of the disclosed subject matter, an apparatus can be provided for performing any of the methods disclosed herein. In embodiments of the disclosed subject matter, a controller can be programmed to implement any of the methods disclosed herein. In embodiments of the disclosed subject matter, a computer readable medium can have recorded instructions for implementing any of the methods disclosed herein.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 1A and 1B show a support structure that encases a fluid circuit and guides any leaks to a leak detector, according to embodiments of the disclosed subject matter.

FIG. 1C shows a fluid handling device with features for supporting and engaging an encased fluid circuit according to the embodiment of FIGS. 1A and 1B.

FIGS. 4A through 4C show features of encasing structures which permit access to a fluid circuit portion while providing for guiding leaks to a leak sensor according to further embodiments.

FIGS. 6A and 6B show a permanent housing that contains links and detects the leaks for a fluid circuit according to an embodiment of the disclosed subject matter.

FIGS. 6C and 6D show a permanent housing that contains links and detects the leaks for a fluid circuit according to another embodiment of the disclosed subject matter.

FIGS. 13 through 18 show fluid circuit support embodiments and features thereof to illustrate subject matter that, among other things, protects tubing against kinking and injury to the tubing and facilitates packaging.

DETAILED DESCRIPTION

Figure 2:
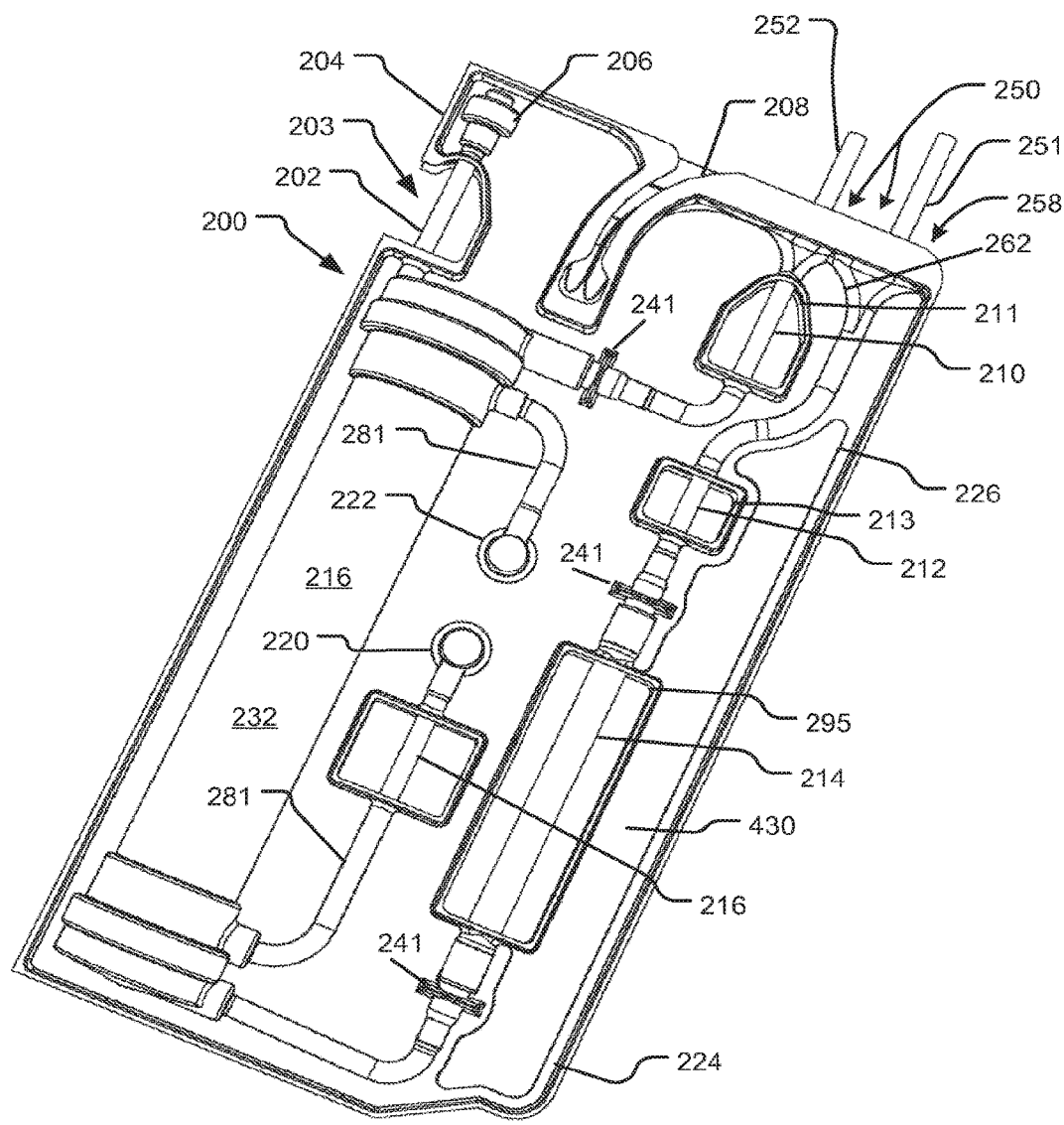
FIG. 2 shows a show a support structure that encases a fluid circuit and guides any leaks to a leak detector according to another embodiment of the disclosed subject matter.

Referring to FIGS. 1A and 1B, a support structure 102 is a folding article of manufacture that is configured to enclose at least portions of one or more fluid circuits 101 so as to contain leaks and guide fluid from a leak at any point in the fluid circuit 101 to one or more locations where a sensor can detect the leak. Tube segments of the circuit may be enclosed by trough channels 128 and recesses of other shapes configured correspondingly to enclose other features of the fluid. In the illustrated embodiment, the support structure 102 has a living hinge portion 136 and various recesses such as recess 114 and cutouts such as 110, 116. The fluid circuit 101 has tubing sections 122 and 124 and other components, such as a treatment component 120, which are supported in respective parts of the support 102 by molded troughs 112 which surround the tubing sections 122 thereby containing leaks and helping to convey them. When the support 102 (originally in a configuration such as discussed with reference to FIG. 3B) is closed in the fashion of a book about the hinge portion 136, it forms a sealed container except for access windows discussed below.

Recesses 114 enclose opposite sides of a treatment component 120, which may be, for example, a filter, a dialyzer, hemofilter, absorbent, oxygenator or other device. Cutouts 110, 116 expose portions of the fluid circuit 101 such as a tubing section 124 for pumping, allowing it to be engaged by actuators or sensors of a machine 150 with which the support structure engages (see FIG. 1C and attending discussion). Flow guides 128 may also be molded into support structure 102 to guide leaking fluid toward the hinge portion 136 which may further guide leaks toward a leakage sensor 106 or a portion 132 of the support structure 102 where a leak sensor may be disposed to detect leaks. These flow guides may be in addition, or alternatively, to the troughs that enclose tubes and other recess features that contain fluid circuit elements. In addition, or alternatively, leaking fluid may be guided by a space between the flat portions 123 of the support structure 102 such that there are seams inter-attaching the facing flat portions (as indicated at 123, for example) of support structure 102.

Figure 7A:
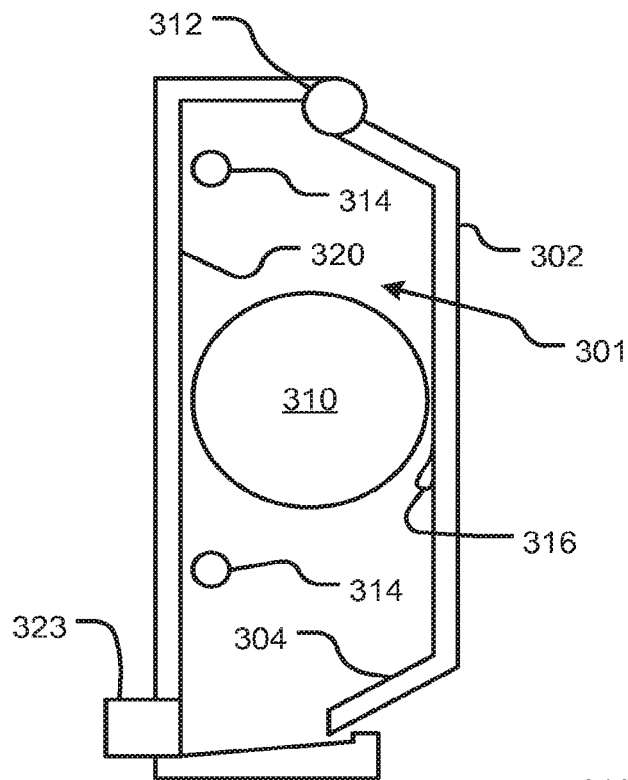
FIGS. 7A and 7B show an embodiment of a housing that contains links and detects the leaks for a fluid circuit which is configured to support a support structure that encases the fluid circuit and guides any leaks to a leak detector and a fluid circuit without an encasing support, respectively.
Figure 7B:
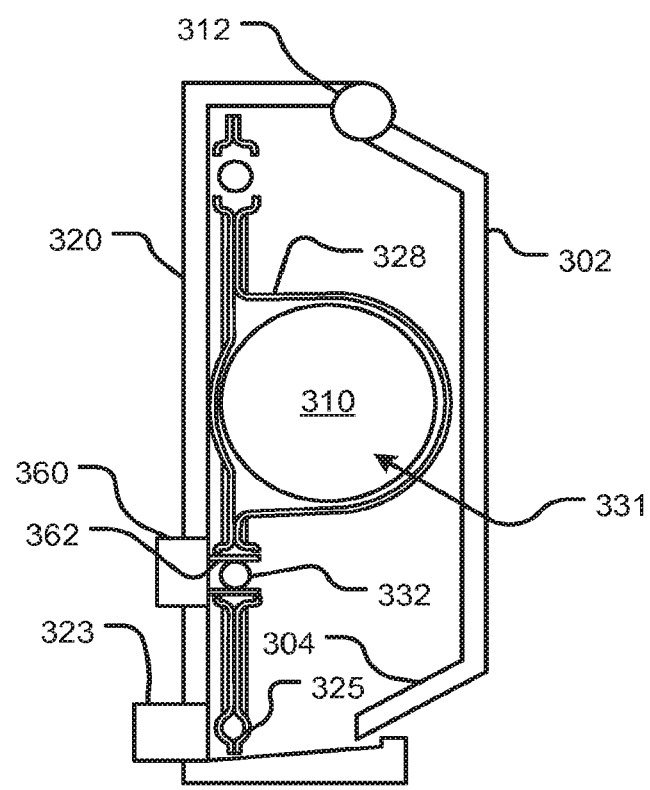

The support structure 102 may be configured with a leak sensor 106 forming part of the support structure or it may convey fluid to a portion 132 of the support structure 102 where an external leak sensor can be disposed (not shown in the present figure but see discussion of FIG. 7B, for example). As shown in FIG. 1B, the support structure 102 may be installed on a treatment machine (not shown) having sensors and actuators as well as connectors to other fluid sources and sinks. The support structure and treatment machine may be configured to hold the support structure at an angle with respect to the direction of gravity such that leaking fluid falls toward the sensor 106.

As shown in FIG. 1C, a fluid handling machine 150, for example, a blood treatment device, may have a fixture 152 configured to receive the support structure 102. The arrangement of the fixture 152 may be such that the component parts of the support structure are oriented and aligned with sensors 158, 154, and actuators 156 and 160 of the machine 150. In an example embodiment, the blood treatment machine may have pump and valve actuators and pressure, temperature, and leak detection sensors. The fixture 152 may be a recess in a face of the machine, for example, that receives the frame of the support structure 102 to hold it in a specific position and orientation. Actuators and sensors may move with respect to the machine 150 to engage the elements of the fluid circuit 101 held by the support structure 102. In the illustrated embodiment, a leak sensor 154 is positioned at a lowest position in order that gravity may drive all leaking fluids toward it. In embodiments, the fixture 152 may include a recess that captures and guides fluids to the leak sensor 154 in case some breach the enclosing structure.

The machine 150 may be configured with a controller 109 and measurement indicators such as a display output for a computer display that indicates leaks when detected. Alternatively the machine 150 can be configured with one or more annunciators 108 that may be used to generate an alarm output upon detection of a leak. Alternative outputs include data signal such as a digital signal containing a message. Other alternative outputs may be employed including automated phone (e.g. cell phone) messages to a call center, data log outputs and other output signals. For a leak detector that forms part of the support structure 102, the location indicated at 154 may represent electrical contacts or a magnetic pickup configured to receive an indication from the sensor (e.g., as indicated at 106 in FIGS. 1A and 1B) and convey a leak indication signal to the 109 controller of the machine 150. The controller 109 manages these functions and which may be integrated in the machine 150, and may include a digital controller employing a variety of known devices and methods. Systems and types of outputs and alarms as well as devices and systems for generating them are described in the incorporated references identified above.

Many other kinds of elements may be included in the fluid circuit 101 and the illustration is merely figurative to highlight certain features of the device. FIG. 2 shows a configuration of a support device 200 (essentially an embodiment more generally represented by the embodiment of FIG. 1A) made from a panel 204 that may be folded or cut into two halves and welded together (the precise manner of assembly is merely a peripheral incident of the embodiment and not essential to the claimed subject matter except as recited by the claims) to enclose a fluid circuit (portions of which are visible at 210, 214, 216, 252, and 251, according to an embodiment of the disclosed subject matter (See also FIG. 3B). The present example of a support device 200 encloses a portion of a blood handling circuit for a dialysis system. The support device 200 foldable panel 204 structure as shown in an unfolded configuration at 271 in FIG. 3B and shown in a folded configuration in FIGS. 2 and 3A. The general features of the present embodiment may be as described with reference to the embodiments described with reference to FIGS. 1A and 1B. More detailed features are shown in FIGS. 4A-4D, 5A-5C, which are discussed below. The treatment unit 216 may be, as in the present embodiment, a dialyzer filter 216 (but could also be a hemofilter, blood oxygenator or the like).

A venous blood line 210 is exposed as shown by the support device 200. An arterial line as indicated at 212 is also exposed by the support device 200. The blood lines 210 and 212, exposed by openings 211 and 213, respectively, are thereby enabled to engage sensors such as a pressure sensor and/or temperature sensor, or a bubble sensor on a fluid handling machine (e.g., 150). Another portion 216 of the fluid circuit is exposed for engagement with a blood component sensor, for example, one that detects leakage of blood into the dialysis fluid which is conveyed by the portion 216. A pumping portion of the arterial line 214 is exposed by a window 295 of the support structure 200 to permit its engagement with a peristaltic pump actuator of the fluid handling machine 150. The exposed portions may engage sensors or actuators such as blood leak detectors (optical type) or pressure sensors, or air detectors or pumps. Interfaces to pressure sensors may be provided inline to respective tubing segments for measurement of venous line pressure, and upstream and downstream of the pump tube segment 214 as indicated at 241.

In the embodiment shown, the dialyzer filter 216 has an air vent 206 stemming from a tube 202 exposed by a cutout 203 in the support 200. The exposed tube 202 may be clamped by an integrated automatic clamping device controlled by a controller of a compatible treatment machine with features as discussed with reference to FIG. 1C. The exposed segment of tubing 202 may be used by the treatment machine to detect fluid as well as to permit an automatic clamp to stop the flow of fluid. Air vent 206 may be used to release air during priming of the blood circuit. Air collects in the header of the filter as described in U.S. Pat. No. 7,544,300, which is also hereby incorporated by reference as is fully set forth herein. As priming fluid is flowed through the blood circuit during priming, air emerges from the vent 206 (a hydrophobic membrane-sealed port) displaced by fluid until the fluid enters the tube segment 202 and is detected. Then the tube segment 202 is clamped. If the retreat of the fluid column occurs due to the accumulation of air in the tube segment 202, and the air retreat of the fluid detected by a fluid detector, then the clamp may be released to vent the air.

Right-angle connectors 220 and 222 interface with a dialysis circuit in an embodiment of the machine 150. When the support 200 is inserted on a treatment device (embodiment of machine 150), the right-angle connectors 220 and 222 automatically connect to source and drain connectors on the machine. These types of connectors may be used to interconnect a non-disposable portion of a fluid circuit, such as the non-blood circuit of a dialysis system, with the disposable portion. In embodiments, the non-disposable portion handles fresh and spent dialysate. The connectors may be needle-less ports (blunt stubs that insert into self-healing septa in the right-angle connectors 220 and 222).

Figure 3A:
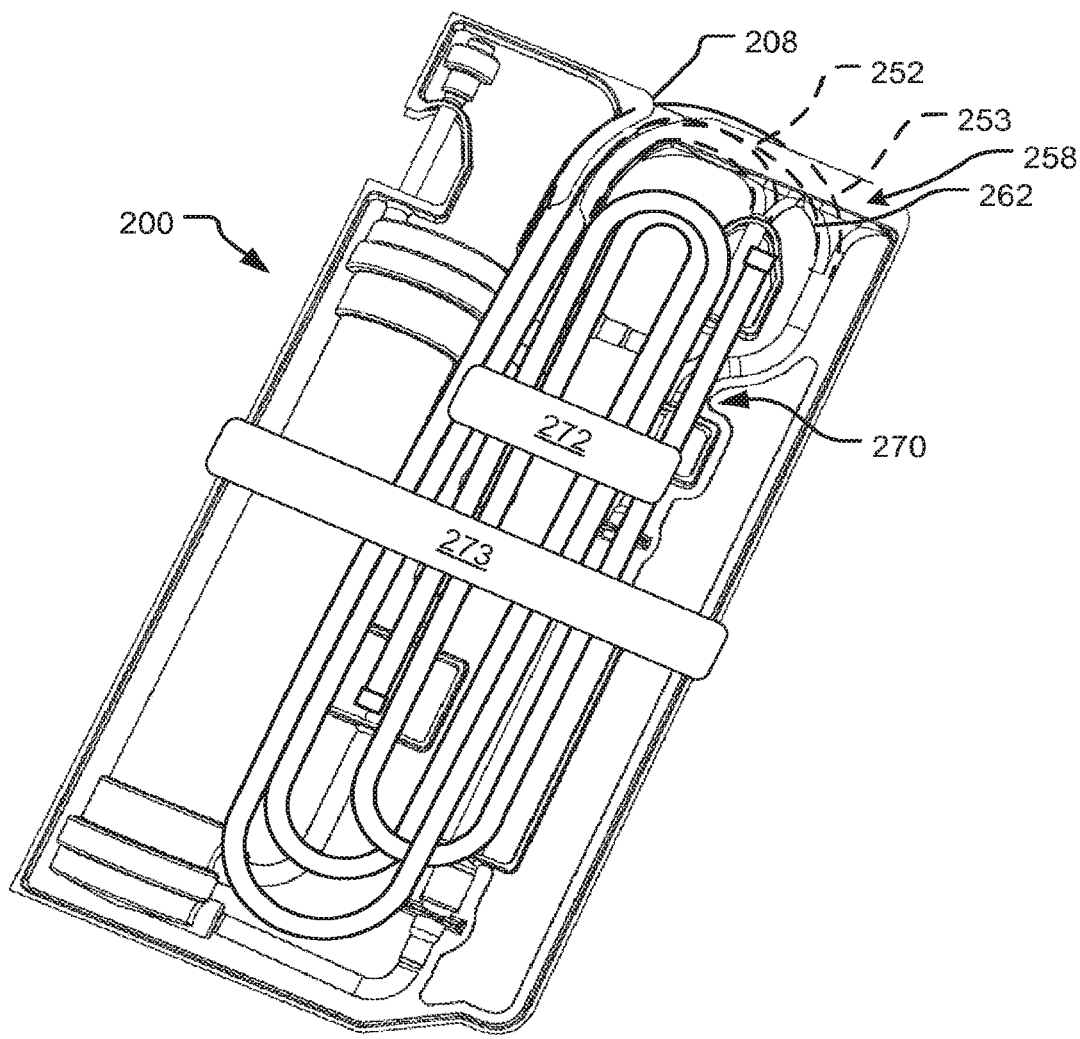
FIG. 3A shows the embodiment of FIG. 2 in a configuration for packaging where tubing lengths that form part of a fluid circuit are coiled to form a compact bundle wherein features of the supporting structure help to prevent tubing kinks in packaged fluid circuits.

Referring now also to FIGS. 3A and 4C, a curved slot 208 allows long stretches of blood tubing 251 and 252 to be inserted therethrough so that tubes 251 and 252 do not kink. The curved slot 208 has a pair of troughs 265 that face toward the slot 208 and curves up toward the viewer to allow the distal extent of the blood tubing 251 and 252 to extend toward a patient access end as shown in FIG. 3A. The distal extents of the tubing 251 and 252 can then be looped and then coiled into an oval and laid over the support 200 as shown in FIG. 3A. It can be seen in FIG. 3A that tubing 252 and 253 are also supported by a horn shaped opening 262 with a curved supporting surface that also helps to prevent kinks. In embodiments, the supporting curved surface 262 and the supporting troughs 265 form a single continuous surface that prevents kinks. The curved slot 208 is defined by overhanging portions 209 that retain the tubes 251 and 252. The size of the curved slot 208 and the choice of materials for the overhanging portions 209 are such that tubes can be snapped into the troughs 265 one at a time and then retained by the overhanging portions 209.

In an alternative embodiment, the curved support 262 lie adjacent a retention mechanism that allows the distal part of the tube to be released by pulling in a direction parallel to the general plane of the support device 200. For example, the configuration of FIG. 15, discussed below, has a gap 645 or 646 into which the distal part of the tube can be retained within the perimeter of the support device as discussed with reference to FIG. 15, below.

The openings through which tubes 251 and 252 extend have axes that are generally in a plane of the support, which is generally planar in shape. The support 200 defines a trough 258 which protects the tubing 251 and 252 when resting therein as shown in FIG. 3A. The tubing may be protected by being at least partly within the perimeter when routed as shown in FIG. 3A but even if the tubing extends slightly beyond the perimeter, if an object forces the tubing, such as when the support and circuit are pushed into a tight box, the tubing will be pushed into the trough 258 until the object encounters the perimeter and no further so that the tubing will still be protected. Thus, the tubing may at all points reside substantially within the perimeter, though not literally, and still be protected by the support device 200.

The two panels making up the support device embodiment illustrated may be of sheet material that defines a single valued surface function such that it can be formed on, and released from, a vacuum mold or other two-part mold. Features of the support 200 may be applied to other types of fluid circuit support structures that do not enclose the circuit to capture leaks. For example, an open panel or simple frame may provide the tubing guides and protection features described above. These features may allow compact packaging without the risk of tubes being injured or kinked as a result of being tightly fitted in packaging, containers, or confined or forced against other objects.

By packaging the support 200 with the blood tubing with the disclosed configuration, kinked tubing can be avoided in packaged fluid circuits which can avoid the flow restrictions created by kinks. Also, kinks can increase the risk of thrombogenesis due to turbulence induced in the wake of the flow restriction caused by them. The openings through which the blood tubes 252 and 251 emerge may be shaped as the horn-shaped opening 265 with the supporting curved surface 262 providing a smoothly curved support on both sides for the blood tubing thereby further preventing kinks. The looping is illustrated at 270 in FIG. 3A. The coil of tubing may be restrained with a band 272 such as a rubber band or tape. The coil may be taped or banded to the support 200 by the same or another such band 273. Other restraints may be used to position the coil as shown. For example, see discussion below of FIGS. 13 to 17. Another feature of the present and further embodiments is the distal part of the tubing may be confined within the perimeter of the support device 200 such that no part of it can get trapped between the support and an external object. This helps safeguard against injury to, or kinking of, the tubing during shipping, storage, or other handling.

Figure 3B:
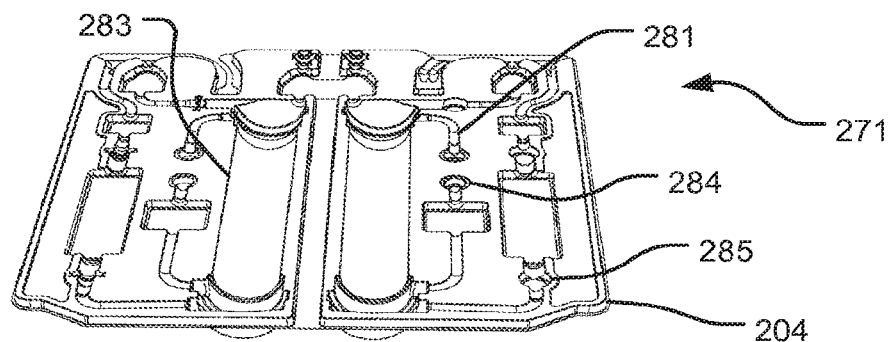
FIG. 3B shows an encasing portion of the support structure of FIG. 3A in an unfolded configuration as may be formed by vacuum molding of thermoplastic.

Referring also to FIGS. 3B and 4A, the panel shaped structure 271 has recesses 283 (one on either side with one indicated at 283) that enclose the fluid circuit as shown in FIG. 2 when folded. The structure 271 has corresponding trough-shaped recesses 281 for tubes, recesses 284 for connectors, and recesses for 285 for sensor elements. FIG. 4A shows a pressure pod 291 visible through an opening 276 and a connector 287 visible through an opening 277. Also shown is an opening 289 for a tubing segment 294. These fluid circuits are representative of elements that may interface with external devices. Corresponding elements may be provided to enclose (fully or partially) and any other elements of a fluid circuit to form the enclosed structure 200. The panel shaped structure 271 may be formed from thermoplastic in a vacuum molding process followed by die-cutting or any suitable process. After folding seams (or other interconnections) may be welded or attached by solvent bonding or adhesive or other suitable process. Instead of folding, the structure 200 may be formed using separate panels or other support elements. Referring to FIG. 4B, a slot shaped opening 275 may expose a tube segment 274 for engagement with an actuator or sensor parts of which lie outside the frame of the support structure.

Figure 5A:
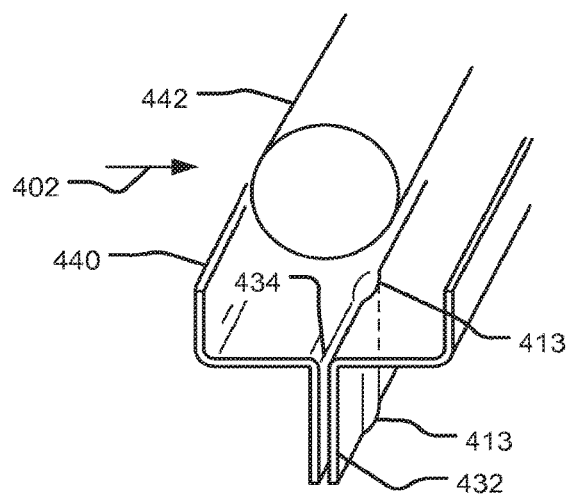
FIGS. 5A through 5D show features of encasing structures which permit access to a fluid circuit portion while providing for guiding leaks to a leak sensor, according to embodiments of the disclosed subject matter.
Figure 5B:
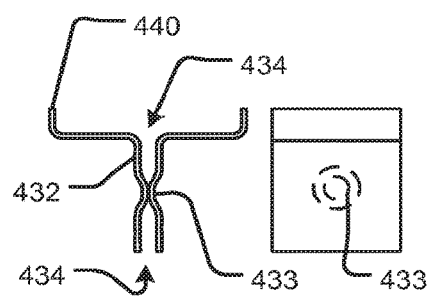
Figure 5C:
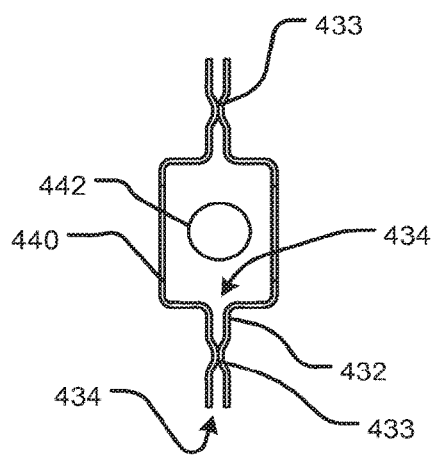
Figure 5D:
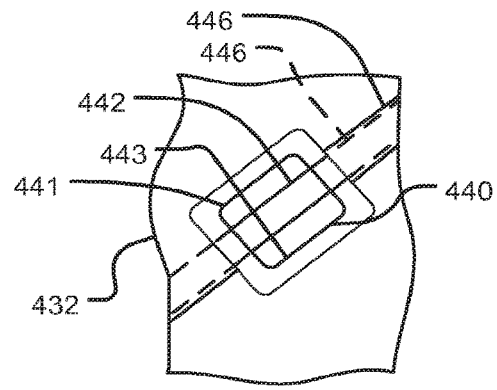

The support device 200 may be configured to enclose enough of the circuit element to minimize the risk of leaks escaping while permitting circuit elements to interface with the fluid handling machine (e.g., 150) and to guide any leaking fluid to a fluid leak sensor (for example, the integrated one indicated at 106 in FIG. 1A). FIG. 5A shows a perspective view of a window of the support device 200, for example, a window 213 as shown in FIG. 2. FIG. 5B shows section and side views of the configuration of FIG. 5A. FIG. 5C shows a window such as 213 in section with both the top and bottom of the frame in section view. FIG. 5D shows a window structure in which a rectangular frame is angled which may assist in the flow of leaking fluids through a support device such as 200. The support device 200 panels 432 may be configured to provide channeling for leaking fluid. In one embodiment, the panels 432 are welded together at dimpled points 433 which ensure a gap 434 between them is provided for leaking fluid to be conveyed between the panels 432 to a leak sensor. The perimeter edges (indicated at 430 in FIG. 2) may be welded or adhesively bonded to ensure fluid cannot leak from the support structure 200. Extension features 440 span a fluid circuit feature, such as a tube 442, that is open for access (access direction indicated by arrow 402) by actuators or sensors of the machine 150 to ensure that fluid leaking from the feature is captured. In additional embodiments, channel structures may be formed into the support structure 200 such as channel 413 indicated in FIG. 5A. A rectangular window 440 that is angled with respect to gravity may provide advantages in terms of ensuring against the escape of fluid flowing around the window 440. For example, rather than dripping from an upper edge 441 to a lower edge 443, if the window 440 were straight, fluid may flow along the upper edge 441 and down around the window 440.

Referring now to FIGS. 6A and 6B, an enclosure 300 is configured as part of a fluid handling machine with actuators and sensors generally as discussed with regard to the foregoing embodiments. In the present embodiment, a fluid circuit 301 is encased in the enclosure 300. For example the fluid circuit 301 may have tubing portions 314 and other elements, such as a cylindrical structure 310, which may be a dialyzer or any of the other components described in the foregoing embodiments. The enclosure includes an access hatch 302 to provide access to an interior of the enclosure. The access hatch may pivot on a hinge 312 by which it is attached to a back panel 320. The configuration is shown in a closed position for operation in FIG. 6A and a partly open position in FIG. 6B. The back panel 320 and/or the hatch may carry sensors, actuators, and/or other devices that interconnect with the elements of the fluid circuit 301. The internal surface of the enclosure has surfaces 321 and 304 that are configured to capture and convey any leaks to a leak sensor 322. The surfaces 304 and 321 may be sloped so as to cause any drips of fluid (as indicated for example at 316 and 317) to flow toward the leak detector 322 and accumulate there as indicated at 318. In the embodiment 300, the surfaces 321 and 304 are shaped such that any fluid accumulating on the hatch 302 drips so as to flow to the fluid sensor 322. This can be accomplished without forming a seal between the panel 320 and the hatch 302, for example, if the hatch 302 fits partly inside a recess 307 of the enclosure 300. A sloping portion 305 may further ensure that fluid moves toward the fluid sensor 322. In a similar arrangement, shown in FIG. 6C, a back panel recess 340 receives a hatch 342 with an internal surface configured similarly to that of the FIG. 6A, 6B embodiment. In the present embodiment, however, the hinge 344 is remote from the edge of the hatch 342. As in the previous embodiment of FIGS. 6A and 6B, containment of leaks and their conveyance to a detector is provided without a seal between the recess 340 and hatch 342.

FIG. 7A shows the embodiment of FIG. 6A with a fluid circuit 301 that is not enclosed in a support structure such as support structure 200 shown in FIG. 2. In the embodiment of FIG. 7A, a leak sensor 323 employs a non-wetted type of detection sensor, such as one that employs an optical, capacitive, induction or some other non-contact mechanism for detecting fluid. In an example embodiment, the sensor 323 is an optical sensor that detects blood, such as the type used in blood treatment system to detect the presence of small amounts of blood in a clear fluid. FIG. 7B shows the configuration of FIG. 7A with an enclosed fluid circuit having a support structure essentially as described above, for example with reference to FIGS. 1A and 2. A support enclosure 328 supports and encases a fluid circuit 331. At 360 a sensor or actuator is shown with engagement portions 362 that engage a fluid circuit portion 332, for example a tube portion. The support enclosure has a lower portion 325 where leaking fluid may collect which is immediately adjacent the fluid sensor 323. Thus, as illustrated in FIG. 7B, the same configuration can accept both enclosed an unenclosed fluid circuits and detect leaks both.

Figure 8:
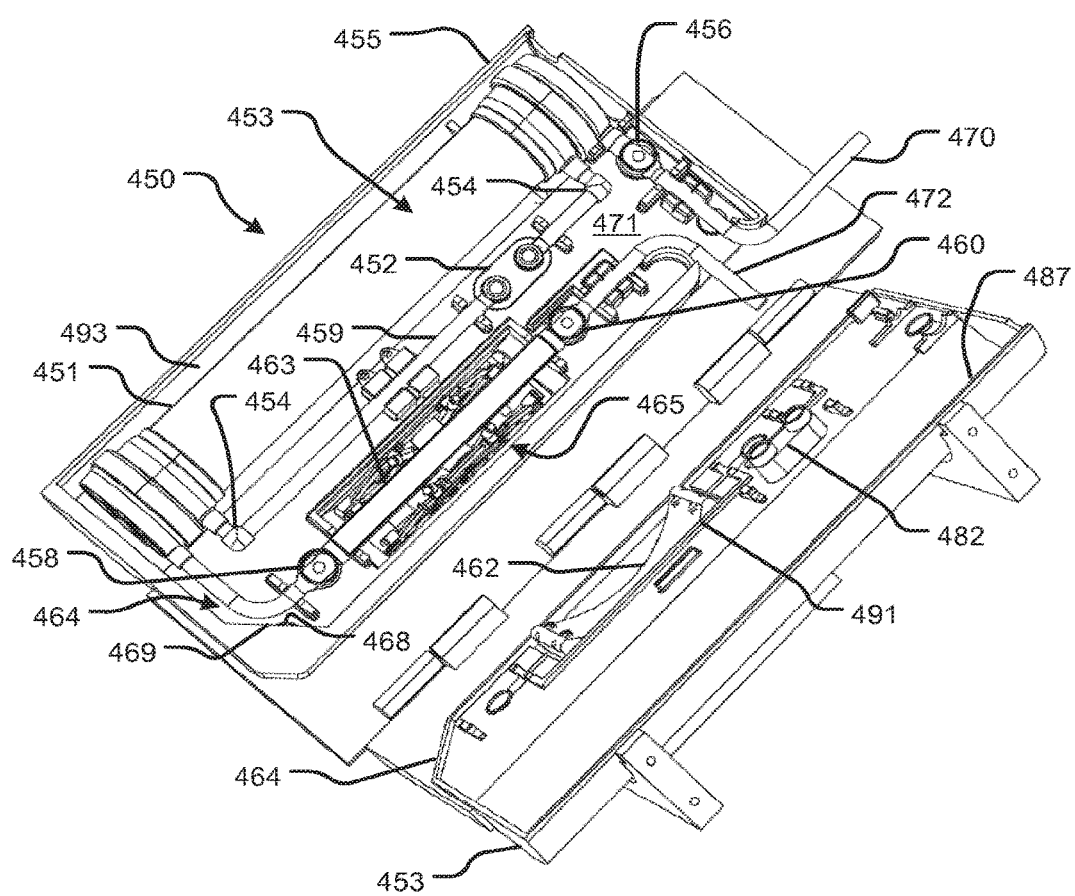
FIG. 8 shows a further embodiment of a permanent housing that contains links and detects the leaks for a fluid circuit, including fluid handling component such as sensors and actuators.

Referring now to FIG. 8, an embodiment of an enclosure 450 for a fluid circuit 453 which is generally similar to the foregoing embodiment 300 in that it contains leaks from fluid circuit 453 elements and conveys any leaking fluid to a fluid sensor 468. An actuator/sensor assembly 455 has various components to engage with components of the fluid circuit 453. Specific features of the present embodiment permit ease of installation of the fluid circuit 453 to the components of the fluid circuit 453. A pair of right angle connectors are formed as a single connector component 452 to facilitate connection to a dialysis circuit behind it (not shown in the figure). Elbows 454 help to auto-align the tubing 459 and the intermediate connector component 452. Pressure pod 456 inserts directly into transducer components in a backplane 471. Pressure pods 458 and 460 insert directly in respective transducers in the backplane and in doing so, align pump tube segment 463 with a peristaltic pump rotor 465. When a door 453 is closed, a constant force retaining member 482 holds the connector component 452 against the hidden mating connectors in the backplane 471. The door 453 has a spring-biased pump race 462 that engages the pump tube segment 463 between itself and the peristaltic pump rotor 465. A filter 451 is received in a trough 493 and enclosed by a closely-conforming opposing shell part 487 of the door 453. A ridge 464 is received into an opening 469 of identical shape ensuring that any fluid that strike the interior of the door 453 are conducted to an interior cavity 464 where the optical sensor 468 faces inwardly.

In any of the foregoing embodiments, a leak sensor may employ any suitable technology for detecting leaks, including optical detection, capacitance, conductance, or any other property may be detected.

Figure 9:
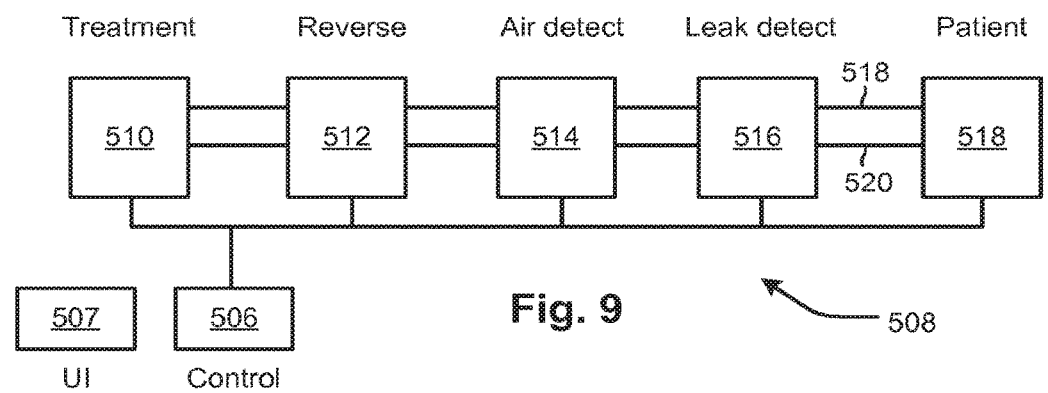
FIG. 9 is a schematic of a fluid handling system with features configured for leak detection, according to embodiments of the disclosed subject matter.

Referring to FIG. 9, a blood treatment system 508 has a blood treatment component 510, a blood flow reversal component 512, an air infiltration detection component 514, and a leak detection component 516 connected to a patient 518 by arterial and venous blood lines 518 and 520, respectively. In operation, the blood treatment component 510 treats blood and pumps blood in a normal direction which delivers treated blood to the patient and withdraws untreated blood through venous and arterial lines 520 and 518, respectively. If a disconnection of the venous line occurs, air is drawn in due to the negative pumping pressure, and the infiltrated air detected by the leak detection component 516. The detection of air may cause a controller 506 to generate a signal indicating the event, sound an alarm, and/or enable a safety mode of the treatment component 510.

In a prior art system conforming to the description of FIG. 9 except for the additional leak detection component 516, the blood flow reversal component 512 regularly reverses the flow of blood so that any disconnections or leaks arising in the venous blood line 520 will cause air to be drawn into the venous blood line 520 and conveyed to the air detection component 514. A problem with the prior art leak detection scheme is that the patient is subjected repeatedly to blood flow reversal which may be undesirable, for example because it creates patient discomfort or it may add time to the treatment due to the inefficiency of reversing the blood flow repeatedly.

A problem with prior art leak detection mechanisms that rely on pressure measurement of the venous blood line is that in order for them to be sensitive enough to detect nearly all possible leaks, such systems produce too many false alarms. This can lead to so-called operator alarm-fatigue. Alarm-fatigue can result in the reflexive cancellation of alarms to the point that the operator may miss a real leak causing harm to the patient.

In the present embodiment, the blood flow reversal component 512 instead operates in a forward direction unless a leak is indicated by the leak detection component 516. When a leak is indicated by the leak detection component 516, the blood flow reversal component reverses the flow of blood for an interval to determine if a leak is confirmed by the presence of air. In embodiments, the leak detection component 516 includes a pressure sensor that indicates the pressure in the venous line. The controller receives a signal from the pressure sensor indicating pressure of the blood in the venous line 520 and when the pressure signal corresponds to a characteristic signature of a leak, for example, the drop in pressure of a certain magnitude over a predefined interval of time. If the signature is detected by the controller 506, a leak indication is generated by the controller 506 causing it to trigger the blood flow reversal component to reverse the flow of blood. The controller may further be configured such that a leak is indicated only upon the subsequent detection of air infiltration by the air infiltration detection component. That is, the controller will only generate a signal indicating the leak and thereby causing a response such as the sounding of an alarm, and/or enablement of a safety mode of the treatment component 510, if the initial detection by the blood leak detection component 516 is confirmed by the detection of air. Otherwise, the normal flow of blood is resumed.

In general, the present system may defined as one in which:

1. A first indicator of a leak is coupled with a confirmatory leak detection device. In a narrower embodiment, the confirmatory leak detection device is triggered by the sensitive indicator.
2. In a variant, the first indicator is sensitive and tends to produce false positive leak indications when used for detection of leaks.
3. In another variant, combinable with the first and second, the first leak detection device triggers the confirmatory leak detection device a predefined number of times in a predefined period, a leak is indicated by the controller even if the confirmatory leak detection device fails to confirm the leak.
4. In another variant, the confirmatory leak detection device is one which requires a change of machine operating state.
5. In another variant, the change of operating state includes the reversal of blood flow.
6. In another variant, a strong indication of a leak causes the controller to indicate an alarm without confirmation by flow reversal, for example, if the magnitude of a detected change in venous pressure over the predefined interval is beyond a second threshold that exceeds the threshold that initiates the confirmatory leak detection process, the leak is automatically indicated rather than invoking the confirmation process.
7. In variants, the venous pressure is measured directly by measuring pressure in the venous blood line and in another variant, the venous pressure is measured indirectly using a pressure sensor responsive to pressure in the effluent line of a dialyzer or hemofilter.

Figure 10:
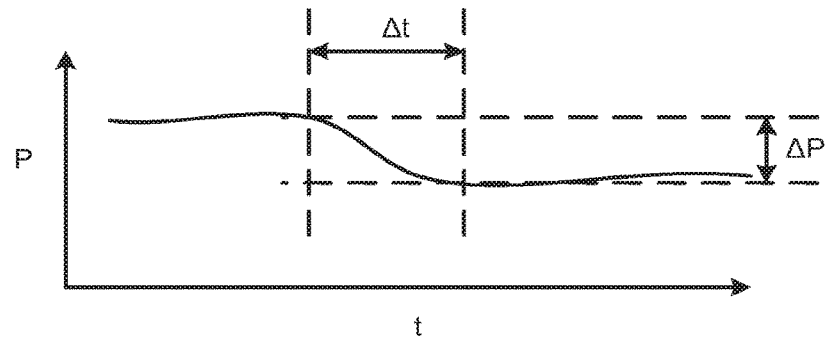
FIG. 10 illustrates a leak detection algorithm that forms part of a leak detection method and system.

The algorithm described for detection of a pressure drop $\Delta P$ in a predefined interval $\Delta t$ is illustrated in FIG. 10. Other leak indicating signatures of the pressure versus time signal may also be employed. It may be noted that the present system allows a very sensitive, and potentially false-alarm-prone, indicator of leaks to be employed without the undesirable consequence of false alarms or the risk of alarm fatigue. In addition, the present system allows the robust method of leak detection by flow reversal to be employed in a minimal fashion that mitigates its undesirable consequences.

The controller 506 may have a user interface 507 that may include, for example, a display. The user interface 57 and controller may be configured to store a log of instances of the sensitive indicator's indications of a leak along with a record of instances of the invocation of the verification operation. These logs may be displayed on the user interface 507 and used for monitoring the treatment operation.

Figure 11:
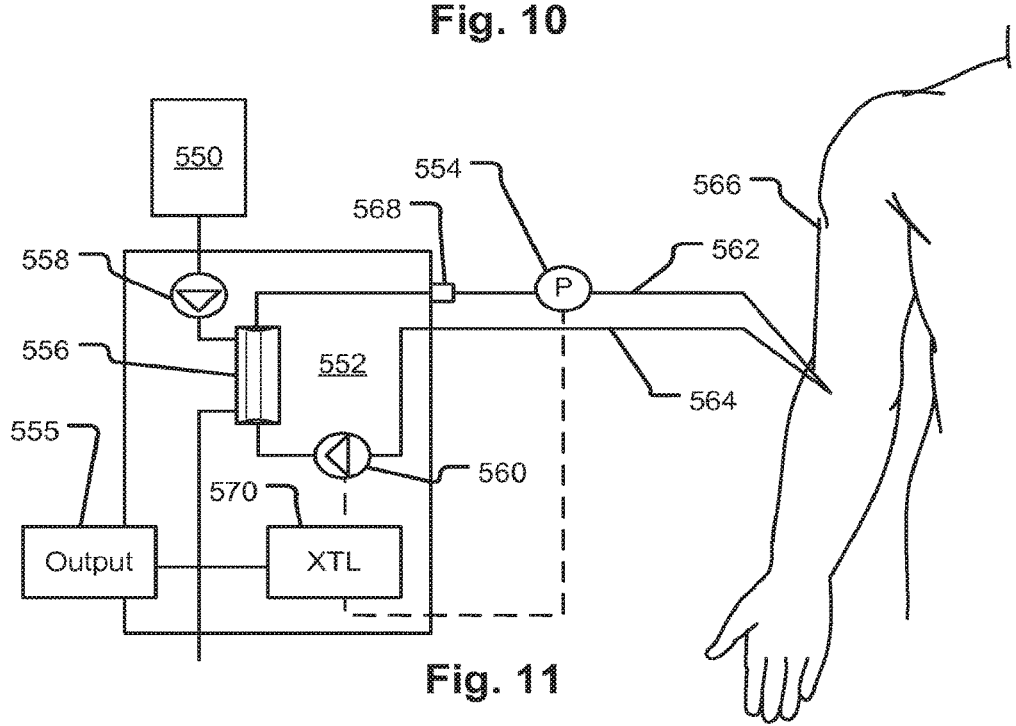
FIG. 11 illustrates features of a blood treatment device which may be used to implement features of the embodiments of FIGS. 9 and 10.

Referring now to FIG. 11, a blood treatment machine has a blood treatment device 556 such as a dialyzer or blood oxygenator. Medicament or gas 550, as applicable, may be pumped through the treatment device 556 by a pump 558 (or flow regulator as applicable). An air detector 568 detects the presence of air in a venous blood line 562. An arterial blood line 564 draw blood from a patient 566 by means of a pump 560. A controller 570 receives a signal indicating pressure indicated by a venous pressure sensor 554. In an embodiment, the venous pressure sensor 554 includes multiple sensors located at various positions with respect to a venous flow path. In another embodiment, the venous pressure sensor is located near the patient access, for example, a pressure pod forming part of a disposable access blood set. When the controller identifies a predefined leak signature, such as may be caused by the accidental withdrawal of a venous access cannula, it controls the blood pump 560 to reverse direction for a period of time. If the controller detects air by the air detector 568, an indication of a leak is generated by the controller 570 which may be applied to an output device 555 and/or initiate a safe mode response by the treatment machine 552.

Figure 12:
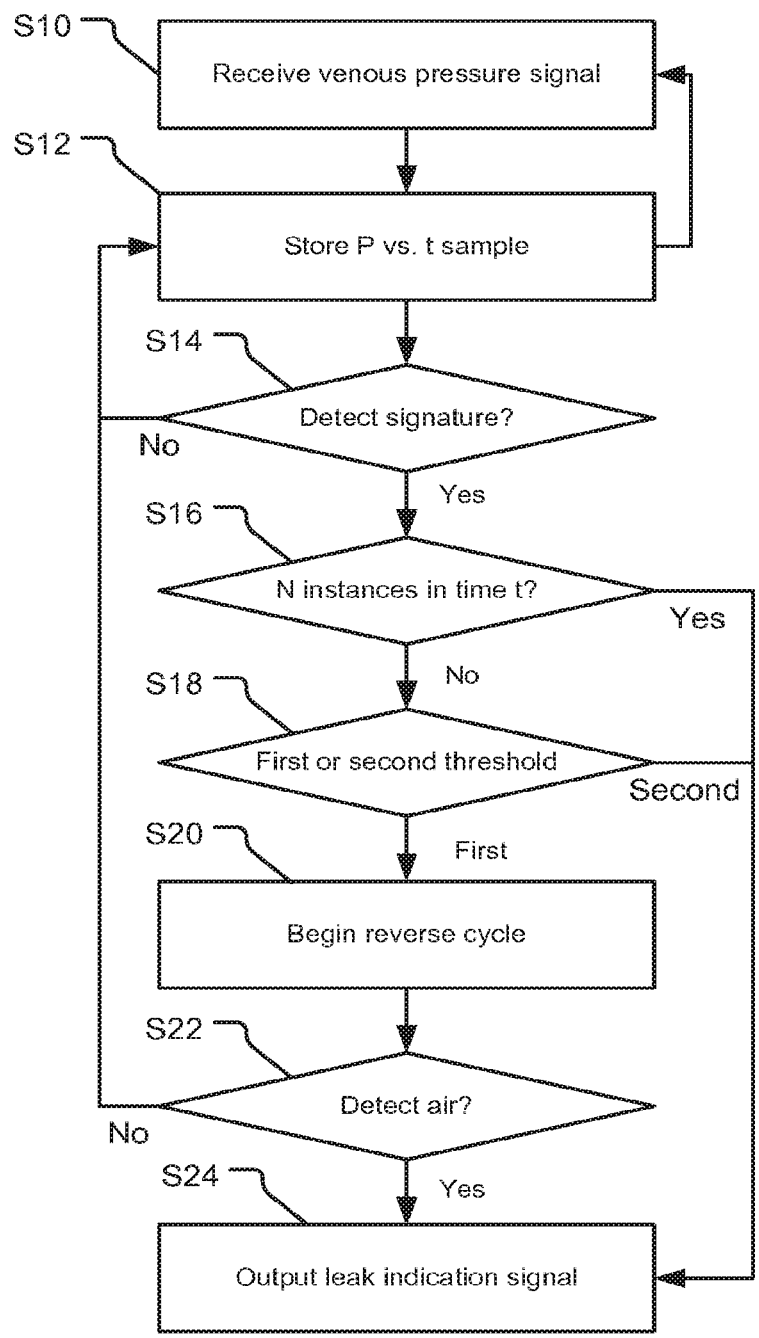
FIG. 12 is a flow chart showing a procedure for a two-stage leak detection system and method according to embodiments of the disclosed subject matter.

FIG. 12 shows a method for detecting a leak according to embodiments of the disclosed subject matter. At S10, a pressure signal is continuously sampled. At S12, the pressure signal samples are stored to generate a pressure versus time signal. The samples may be stored in a buffer to cover a predefined interval of time and a delay may be chosen to provide a desired temporal spacing of the samples. Criteria may be applied for rejecting samples or for filtering the buffered samples to remove ergodic or random noise, for example, pulsations of a pump, patient movement, etc. If a signature is detected in the time series of pressure data generated at step S14, at S16, it is determined if the present indication is an instance of more than a predefined number of instances of signature recognition and if so, at step S24 a leak detection signal is output. If at S16, the number of instance of the signature being recognized in the predefine interval is not exceeded, then at S18 it is determined if the signature exceeds are predefined magnitude or other characteristic indicating a strong probability of a leak, for example, a pressure change of a predefined high magnitude threshold. If the signature exceeds this higher probability threshold then control moves to S24, otherwise, at S20, blood flow is reversed for a predefined period. If air is detected during the predefined period, at S24 a leak is indicated otherwise control reverts to S12.

A signature has been identified from logs of actual patient data which is reasonably predictive of a leak or disconnection. This signature is a pressure loss of 17 mm Hg between two pressure plateaus within a narrow interval of 10 or 15 seconds which may be chosen, for example, responsively to pump speed or nominal flow rate.

In any of the disclosed embodiments, a safe mode may be invoked by the detection and confirmation of a leak, where the safe mode may include outputting an alarm, halting the pumping of blood, generating an automated phone call to a supervising center, reducing a rate of blood flow, clamping fluid lines, taking further corrective action to restore patency to a blood line, and generating a responsive display, for example, one including instructions for correcting a leak.

FIGS. 13 through 18 show fluid circuit support embodiments and features thereof to illustrate subject matter that, among other things, protects tubing against kinking and injury to the tubing and facilitates packaging.

Figure 13:
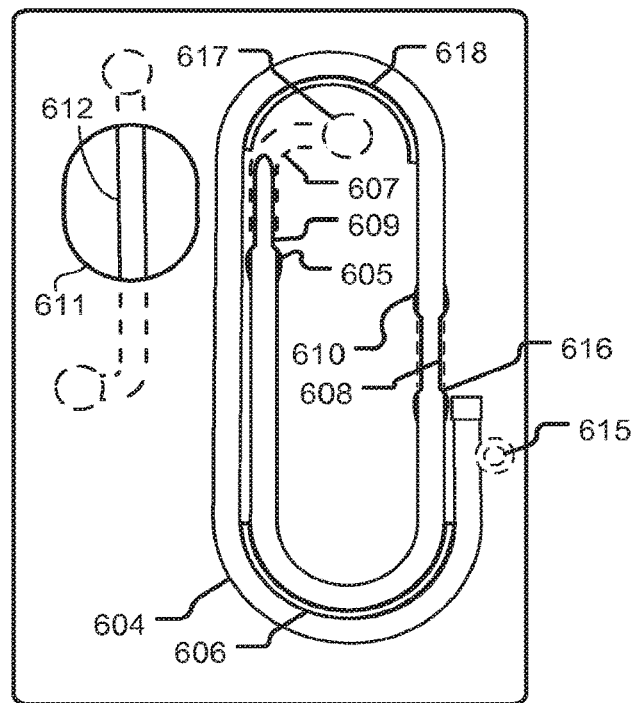

Referring to FIG. 13, a fluid circuit support 602 is of a generally planar form that encloses fluid circuit components of any description, but at least including a tubular portion 604 that extends outside the support 602. For example, the enclosed fluid circuit components may include tubular portions such as indicated at 607 and 612 or other components such as connectors or other devices indicated figuratively at 617. Components may be exposed for engagement with sensors or actuators by openings such as indicated at 611. The support may be formed of molded panels that are affixed to each other by standoff dimples as indicated at 615 or otherwise interconnected to create an internal space in which the internal fluid circuit components may be held. The standoffs may be elongate ridges with continuous attachments (e.g., adhesively bonded, welded, or attached by fasteners) to form a fluid seal as described with reference to the FIGS. 2 and 3A embodiments.

The features shown in FIG. 13 may be employed with any of the disclosed embodiments. For example, a support structure has fence 618 that has a shape whose radius (which may not be constant in embodiments) is selected to prevent a tube 604 from kinking when drawn tightly therearound as depicted. Another fence is shown at 606 which supports the tube 604 both inside and outside. FIG. 16 shows a structure by which the fence 604 or 606 may be created, for example, by vacuum forming. A panel 666A is formed with a ridge 664A to form the fence. A panel portion is shown in section view in FIG. 16. Only one tube 662A is shown adjacent to an outside of the fence 664A. Although the fence is shown with a rectilinear shape, it may be more tapered to facilitate release from the mold. 667A shows a tube portion internal to the support structure similar to 200 discussed above. Reference numeral 660B shows a structure essentially identical structure 660A with similarly referenced elements (except that the letter A is replaced with letter B in the reference numerals). The fence 664B may serve as a support for stacking multiple support structures as shown in the stack portion 660B and 660A. This may allow the support structures to be stacked without applying pressure to the tube 662A outside the enclosed part of the support structure. It may also aid in the prevention of other outside materials, such as packaging or other objects from deforming the tube 662A (662B). Tubes 662A and 662B represent tubes that extend beyond the support structure and which are coiled, for example as discussed above and indicated in FIG. 3A at 270.

Tube 604 is an extension from an internal portion 607 that extends through an opening 604. Although a single tube is shown, multiple tubes may extend from a single, or from respective openings. A slot 609 defines flexible tab portions that overlie the tube 607 partly as it emerges progressively from the interior of the support 602 toward the outside. A support ramp (not shown in FIG. 13 but see discussion of FIG. 17, in particular feature 679) may be provided inside the support 602 to guide the tube upwardly toward, and through, the opening 604. The extended portion of the tube 609 may be routed around fences 606 and 618 as shown. Alternatively, the extended portion of the tube 609 may be looped and tied as illustrated in FIG. 3A. Another form of tube guide has a slot 608 with openings 610 at either end. A tube on the outside of the support 602 can be held in place to help prevent kinking and to help confine the external portion of the tube 604 within the perimeter of the support 602. The feature may be used with or without the fence features.

Figure 14:
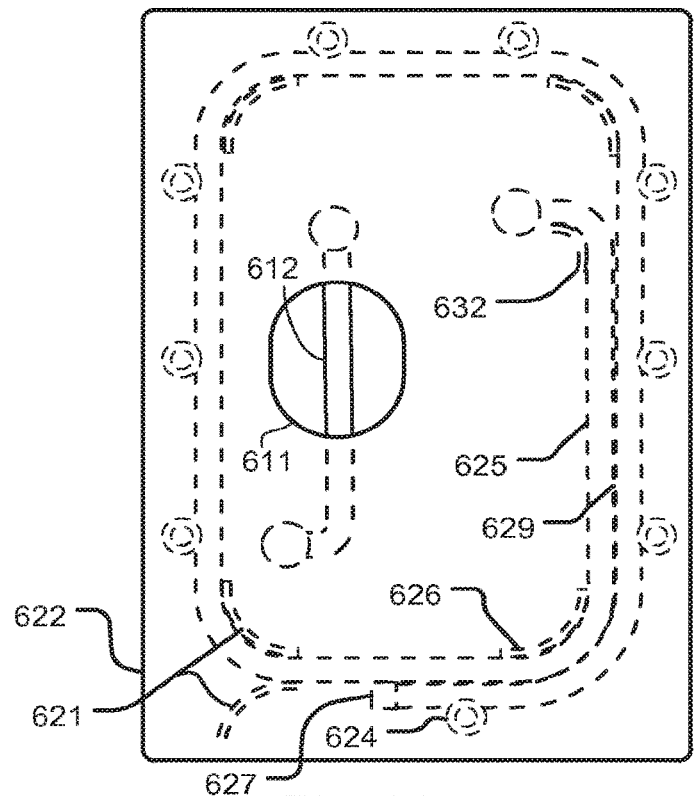

In FIG. 14, an internal tube is routed around a fence of dimples 624 from which the tube 629 can be pulled in a support device 622. FIG. 15 shows a section view of the principle where a tube 653 is held in recess 646 formed by opposing standoffs 655 in respective panels 642 and 643 of a support device. The section view shows internal tube 651 and other circuit element 654 of arbitrary description enclosed between the panels 642 and 643. Tubes 641 and 644 are doubled up in a wider area 648 captured similarly to tube 653. The dimples or standoffs may take the form of elongate features rather than low aspect ratio features shown. Standoffs may be bonded, fastened by fasteners, welded or interconnected by any suitable means. Preferably they are arranged and numbered to provide rigidity to the support structure 622, 602 (also 200 and similar).

The tube 653 (627) end may be pulled out between the dimples 655 (624) that capture it until the drawing may be halted by guides 621, which may be shaped to relieve strain (thereby prevent kinking) if the tube is pulled to the side. Internal guides 626, 632 may be provided along straight and curved sections as required to permit the tube to be wrapped. These guides 626 may be replaced by a continuous fence that runs along major sides of the support device 622 in embodiments. It can be visually confirmed that the tube 629 is held safely within the perimeter of the support 622 so that it can be shipped in tight fitting container without risk of kinking or denting the tubes and also so that the extended portion of the tube is not injured or strained during other kinds of storage or handling.

Referring to FIG. 17, a support structure 677 with attached panel portions 672 and 681 that enclose a tube 683 (and optionally, other elements of a fluid circuit) that extends outside the support structure 677 through an opening 675. The opening may include a curved surface 685 that supports the tube 683. The panel 672 may have a curved support feature 679 as well. A fence 678 is formed around the external face of the upper panel 681 which functions to help retain and protect the external portion of the tube 683 (the external portion being indicated at 674). The lower panel 672 may be attached to an underside of the upper panel 681 by suitable standoff features such as indicated at 676 to create an enclosed space 671 for fluid circuit components.

Referring to FIG. 18, although in the embodiments described above, fluid circuit supports were described in terms of examples that employed interconnected panels. However a variety of different configurations are possible which may offer the benefit of various features of the disclosed embodiments. For example, a framed structure such as indicated at 682 can enclose parts of a fluid circuit and provide an opening through which an external tube portion 684 may emerge. Other features such as guides, strain relieving features, releasable connections etc. may also be provided. The frame (or a panel) may also be provided in a fully open structure, for example, a single panel or a frame with only one side supporting the fluid circuit elements. In the latter case, the fluid circuit elements that do not extend for connection to an outside fluid source and/or sink may be mounted to the support and the extended tube or tubes can be releasably attached to the same side or the opposite side of the support.

Figure 19:
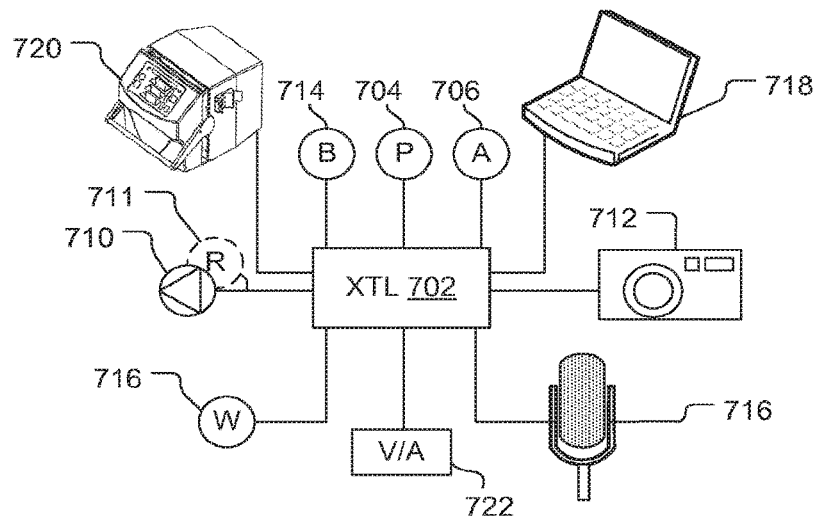
FIG. 19 shows detection and control system features for implementing embodiments of the system and method of FIG. 20.
Figure 20:
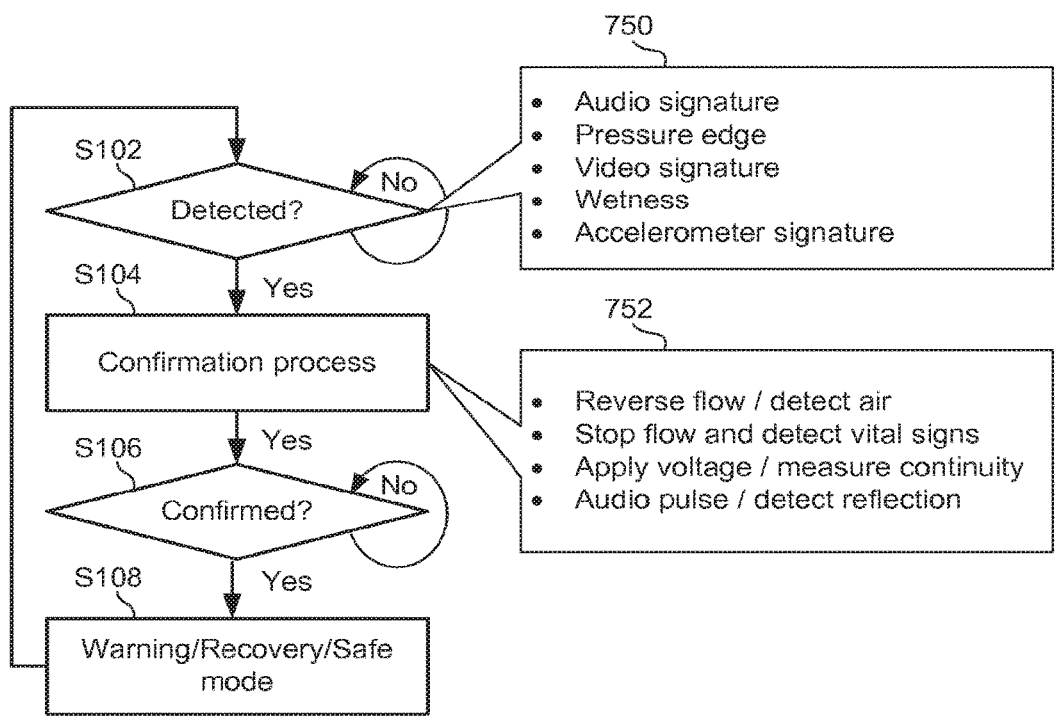
FIG. 20 describes a leak detection method and system and specific alternative embodiments.

Referring to FIGS. 19-20, detection and control system features for implementing embodiments of a system and method according to alternative embodiments of leak detection in a fluid management system are now described. A controller 702 is connected to a user interface 718 configured to receive commands and output data such as error indications, alarms, treatment logs, performance logs, treatment status, etc. A fluid management device 720 has sensors and actuators configured for performing a process such as an extracorporeal blood treatment or other type of operation, such as infusion, plasmapheresis, or peritoneal dialysis. The device 720 may receive disposable components for managing the flow of fluid while ensuring sterility. The controller 702, user interface 718, and further components now described may be integrated in the fluid management device 720 or may be separate components, either connected to it or separate from it. The controller 702 may be one or more controllers that operate independently or are in communication with each other or to a common element.

A pressure sensor 704 receives pressure signals indicating fluid pressure at one or more locations of a fluid circuit engaged by device 720. The pressure signal may represent pressure in a venous line of blood treatment circuit, for example, according to a principal one of the disclosed embodiments. Alternatively it may be a normally-positive pressure line of a fluid circuit such as the return flow line of a peritoneal dialysis circuit. Alternatively, it may be any fluid conveyance channel of a fluid management circuit.

One or more accelerometers 706 may be connected to a fluid circuit (including the peripheral lines), a patient, patient access, and/or a patient's bed or chair. Alternatively, one or more accelerometers may be connected to components of a non-treatment circuit to detect vibrations. Such accelerations may be used to detect configuration changes that might affect pressure signals and lead to misclassification. For example, a patient rolling over in bed may cause a sudden drop in pressure. By applying the accelerometer signal to the controller contemporaneously with the pressure signal from a positive pressure line, the controller may use both signals to classify a leak. In such a case, the accelerometer signal may be used to inhibit the classification of the pressure signal as indicating a leak if the acceleration is experienced contemporaneously with the pressure drop. An accelerometer signal may be classified independently as showing the signature of an event such as striking on object (e.g., an accelerometer attached to a patient access falling out and hitting the floor).

An imaging device 712 generates an image of a scene, for still image capture or video capture, for example. The imaging device may use thermal imaging, optical, ultraviolet, or a combination of the above. The controller may be configured for machine classification of events or configurations of the captured scene. For example, a video sequence indicating a restless patient may be classified as such and a signal output indicating the event class and the timing thereof may be applied to the controller 702. The classifier may recognize a warm or colored blob as a leak of warm and/or colored fluid such as blood and similarly output an indication of an external flow or leak thereof. The image may classify a change in the configuration of a fluid line that indicates a kinked line or a change in the position of a line that may correspond to a pressure fluctuation that is detected concurrently. The indication of the change in the shape of the fluid line (for example, kinked or simply moved) may be used by the controller to aid in the machine classification of fluid line pressure data received by it from pressure sensor 704.

Note as used throughout the specification herein, classifier, classification, and classify may be used to denote machine algorithms for converting one or more inputs to an indicator of a class. The terms may correspond to the simplest classification process which is comparing a raw signal to a predefined range and outputting the result of the comparison. For example, an analog comparator circuit may be a classifier as the term is used herein.

A gas detector 714 may be connected to the controller to detect the presence of gas or air into a fluid line. If a line is under negative pressure, a leak (a type of leak being a disconnection of a patient access) may cause the infiltration of air which may be detected when pumped to an air detector 714. A pump 710 or flow reversing valve 711 may be connected to the controller to implement the flow reversal function discussed above. A wetness detector 722 may also apply a signal to the controller 702 indicating the presence of fluid outside the fluid circuit. For example, electrodes of a galvanometer may indicate the presence of external fluid thereby indicating a leak. The electrodes may be held in an absorbent material such as an absorbent pad under a patient's access so that leaking fluid can form a conductive path in the wetted pad. A microphone 716 may be used to detect ambient sounds that may indicate a leak and/or may disambiguate another signal (e.g. pressure, video, etc.) used by a classification algorithm.

Any and all of the sensor signals described above with reference to FIG. 19 (or elsewhere herein) may be combined by the controller 702 in an event or state classifier to identify an event or state of the system including the classification of a leak. The classification may be done by any of a variety of classifiers such as explicit rule based networks, supervised learning algorithms, unsupervised learning algorithms, neural network, etc. Back propagation classifiers may be trained using treatment log data. In any of the foregoing, the input vector that results in a particular class recognition of a classifier may be identified as a "signature," for example an audio signature might the sound of a needle dropping or a patient rolling over in bed. A video signature might be a growing red blob (spilled blood). A combined input vector of a video sequence and contemporaneous audio sequence may provide a signature of a patient rolling over in bed. A voltage or signal source and signal receiver or galvanometer 722 may be used to detect continuity in a fluid circuit by applying a voltage and measuring a current or by applying a modulated electrical voltage and measuring a current signal across the fluid circuit. This may be used to detect a conductive (e.g., blood or electrolyte) fluid path's continuity. A detection or failure signal may be applied to the controller 702 as well.

Referring to FIG. 20, a general method for detecting leaks includes a first step S102 in which a first one or more signals is analyzed to determine if there is a leak. The first one or more signals may be, alone or in combination, a weak discriminator and thus, to reduce false positives, it may be used to invoke a confirmation process. If a leak is indicated (again, either by a signal or a classifier output responsive to one or more signals), a confirmation process is invoked at S104. An examples is the flow reversal process described above with reference to FIG. 12. Responsively to the confirmation process a refined signal of a leak (or no leak) is generated and used in S108 to invoke a warning signal output from the UI 718 or a recovery or safe mode process of fluid handling device 720. Examples of safe mode include halting pumps and closing valves to prevent continuation of a leak, output of instructions for recovery on the UI 718, and/or an alarm to alert a technician or operator. S108 may be terminal or, with recovery may revert to S102.

As indicated at 750, the initial one or more signals used for step S102 may be, or include, as described with reference to FIG. 19, an audio signature, a pressure signal edge as described with reference to S14 in FIG. 12, a video event signature, wetness indication, or and accelerometer signature. Any and all of these examples may be combined. As indicated at 752, the confirmation process may be, or include, a flow reversal to generate an air detection (for example, as described with reference to FIG. 12).

As also indicated at 752, the confirmation process S104 may also include an operation in which a pressure signal is monitored during operation of the fluid circuit or only at times for the present operation. The configuration or status of the fluid management system is changed to permit the pressure signal to detect a signal that is clearer or detectable only when the fluid management system acquires that status. An example, is cessation of pumping of fluid and monitoring of the pressure in the line connected to a patient for subtle pressure fluctuations indicating vital signs such as breathing and heart beats. The pressure signal may be filtered digitally to remove noise and other external influences and the result applied to a classifier.

As also indicated at 752, another confirmation process includes the application of a voltage to the fluid lines and subsequent detection of continuity with a galvanometer. The technique of using continuity or passage of a modulated signal (the modulation producing a recognizable signature that can be filtered out of background noise) confirms the connection of blood or peritoneal (or other) lines to a patient, which forms a part of the electrical path of the circuit only when the patient access is properly connected. A pressure fluctuation signal, such as a pressure fluctuation in the acoustic range, may also be applied to a fluid circuit to establish continuity. The received pressure fluctuation signal may contain transmitted and/or reflected components which may be used to establish, or suggest, the status of a fluid circuit or a connection thereof.

Figure 21:
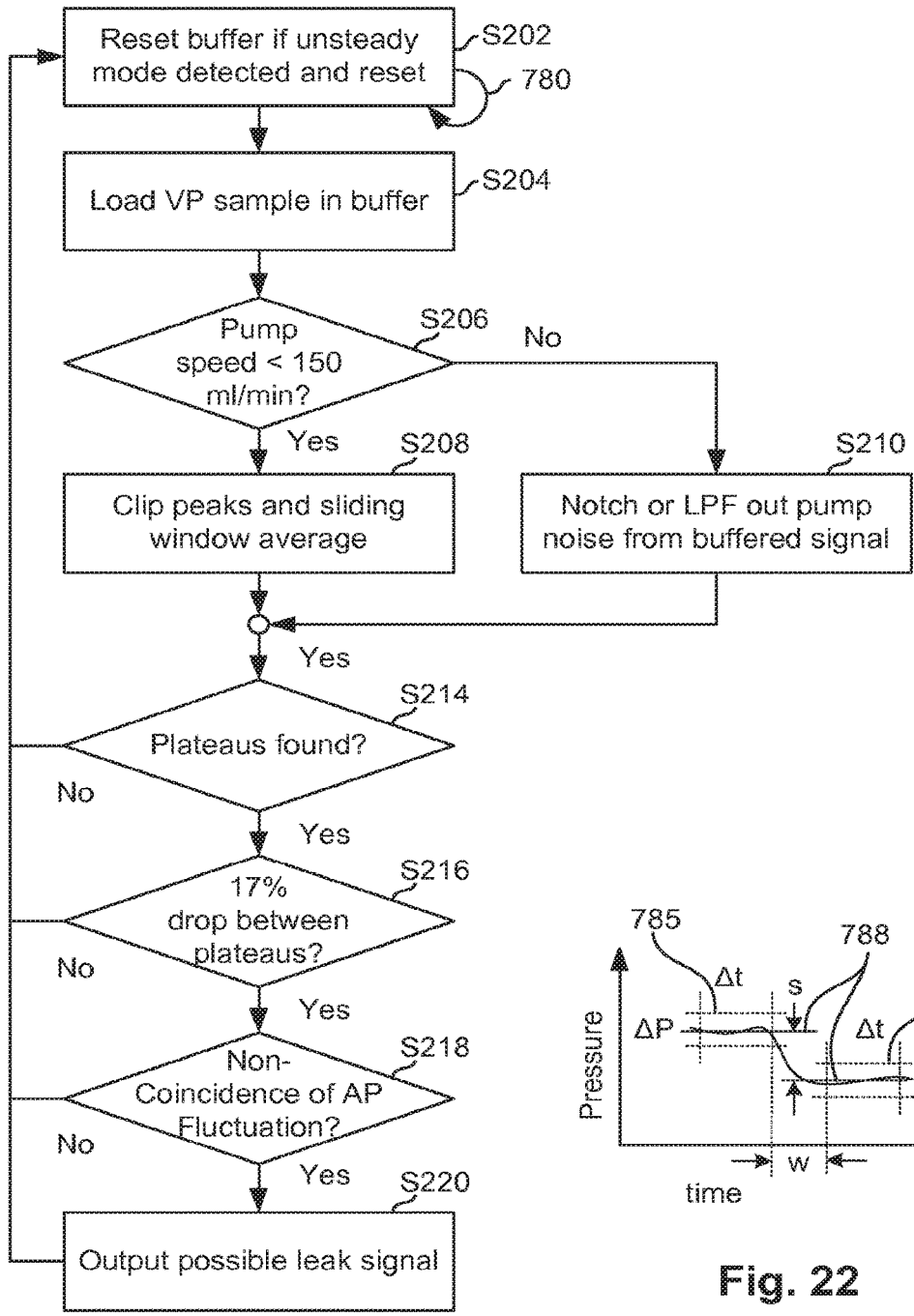
FIG. 21 is a flow chart showing a procedure that may be used for a first of the two-stage leak detection system and method described with regard to other embodiments, for example, in place of S14 in FIG. 12.

FIG. 21 is a flow chart showing a procedure that may be used for a first of the two-stage leak detection system and method described with regard to other embodiments, for example, in place of S14 in FIG. 12. The procedure may also be used as a stand-alone method for detecting a venous line disconnect of a blood treatment system or paroxysmal leak in the venous line. At S202, a buffer is reset by clearing all values of venous pressure and arterial pressure edges stored therein if the blood treatment system is in an unsteady operating mode. The control flow resets if the machine is in unsteady operating mode as indicated by the arrow 780, clearing the buffer at the same time.

At S204, a new venous pressure and arterial pressure sample are loaded into the buffer. At S206 the pump speed (blood pump speed=nominal volume rate of blood flow based on pump speed) determines the type of filter to be applied to the stored stream of arterial pressure samples. At S208, the high and low samples over the previous (in time) 6 arterial samples and averaging the rest so the filter takes a four-sample average of the samples remaining after high and low samples are discarded to form a sliding window function that is applied retrospectively to generate the slow pump filter. At S210, a notch filter is applied to the samples to remove pump noise from the arterial pressure samples. Alternatively, a low pass filter may be applied with a cutoff at about, or below, the pump pulsation frequency. In embodiments, the pump is a peristaltic or reciprocating pump. The venous pressure signal is searched for a current venous pressure plateau and a prior plateau within a prior 60 samples (i.e., 60 seconds). A venous pressure plateau may be defined as one in which the pressure values lie within a predefined range for a predefined interval. At S216 if a pressure change of some predefined amount, for example in the range of 12 to 25%, is identified between detected plateaus, then it is determined if the arterial pressure was stable (within a predefined range of values) during the inter-plateau interval at S218. A pressure change of 17% was found through experiment to provide an optimal discriminator for a known hemodialysis system configuration.

The inter-plateau interval (i.e. window) may be defined responsively to pump speed, with a longer interval for slower pump speeds. If the filtered arterial pressure signal was stable, the controller generates a signal indicating a leak, or possible leak, at S220. A stable filtered arterial pressure is defined as a change of less than 10 mmHg between samples during the inter-plateau interval. At all decision points S212, S214, S216, and S218, control returns to S202 if the determination is negative.

Figure 22:
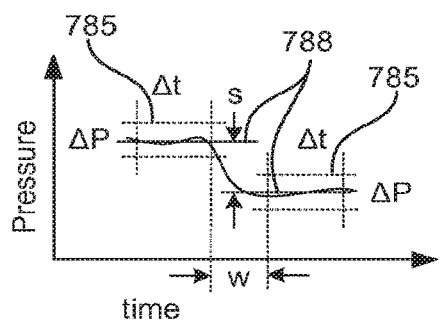
FIG. 22 is a graph illustrating pressure fall detection based on plateau detection and a fall in a filtered venous pressure signal, according to one or more embodiments of the disclosed subject matter.

FIG. 22 illustrates the pressure fall detection based on plateau detection and the fall in the filtered venous pressure signal. The plateau criteria are represented as a box whose height is the predefined plateau pressure range $\Delta P$ and whose width is the predefined plateau interval $\Delta t$. The window (e.g., 10 or 15 samples) over which the pressure fall is required to be found is indicated by "w" and the magnitude by "s." The plateau value averages are indicated at 788 and the difference between them indicated by "s."

In any of the foregoing embodiments, the pressure used to trigger the second stage of the two stage leak detection system may be venous line pressure of a blood treatment system. This pressure may be measured within the blood line of the fluid circuit using a drip chamber, pressure pod, or any other suitable blood line pressure measurement technique. It may be also be measured indirectly by measuring the pressure of effluent that is in contact with the venous line through a filter membrane, such as a dialyzer.

In any of the foregoing embodiments, tubular elements may be replaced with other types of flow channels suitable for conveying fluids. Examples include seam-welded panels forming fluid channels, one or more rigid vessels defining channels therein, rigid or flexible pipe networks, etc.

In any of the embodiments for a fluid circuit and/or support for the same, the portion of the tubing that extends beyond the support device (e.g., 200 or 602 or similar) may be for an infusion line to be extended toward a patient. Also it (or they, in the case of multiple tubes) may be for one or two patient access lines of a blood treatment system. In any of the above embodiments, the fluid circuit may be a disposable unit for use with an infusion apparatus, an extracorporeal blood treatment system, transfusion or plasmapheresis system, blood oxygenator, or any type of medical device requiring connection to a patient, a source or drain, or other connection that must be extended or may be facilitated by having an elongate attachment or more than one.

It will be appreciated that the modules, processes, systems, and sections described above can be implemented in hardware, hardware programmed by software, software instruction stored on a non-transitory computer readable medium or a combination of the above. For example, a method for detecting leaks using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of medical device software and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, leak detection methods, devices and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method for performing a blood treatment, comprising:
   pumping blood to a patient through a first blood line with a blood treatment machine;
   receiving at a controller of said blood treatment machine a first signal indicating a suspected leak in said first blood line based on a first leak detection operation;
   at said controller, responsively to said first signal, commanding a leak verification operation that is different from the first leak detection operation and verifies whether the suspected leak is an actual leak;

receiving a second signal indicating a result of the leak verification operation that indicates whether the suspected leak in said first blood line is verified as the actual leak; and at said controller, generating a leak indicating signal if said second signal indicates that the suspected leak is verified as the actual leak.

2. The method of claim 1, wherein said controller is configured to control a rate and direction of said pumping and said leak verification operation includes reversing a flow of blood in said first blood line and detecting air in said first blood line.

3. The method of claim 1, further comprising:
generating said first signal, wherein said generating said first signal includes detecting a change of pressure in said first blood line.

4. The method of claim 1, further comprising:
generating said first signal, wherein said generating said first signal includes detecting a threshold rate of change of pressure in said first blood line of a predefined magnitude between adjacent intervals where the pressure remains within a predefined stable range.

5. The method of claim 1, further comprising:
generating said first signal, wherein said generating said first signal includes detecting a characteristic of a pressure versus time signal characterizing a flow in said first blood line.

6. A system for performing a blood treatment, comprising:
a blood treatment component including a fluid pump configured to pump blood to a patient through a first blood line; and
a controller configured to control flow of the blood through the blood treatment component, wherein
said controller is further configured to receive a first signal indicating a suspected leak in said first blood line based on a first leak detection operation,
said controller is further configured to, responsively to said first signal, command a leak verification operation that is different from the first leak detection operation and verifies whether the suspected leak is an actual leak and receive a second signal indicating whether the suspected leak in said first blood line is verified as the actual leak, and
said controller is further configured to generate a leak-indicating signal responsively to said second signal.

7. The system of claim 6, wherein said controller is further configured to control a rate and direction of said pumping, and said leak verification operation includes reversing a flow of blood in said first blood line and detecting air in said first blood line.

8. The system of claim 6, wherein said controller is further configured to generate said first signal responsively to a detection of a change of pressure in said first blood line.

9. The system of claim 6, wherein said controller is further configured to generate said first signal responsively to a detection of a rate of change of pressure in said first blood line.

10. The system of claim 6, wherein said controller is configured to generate said first signal responsively to a detection of a characteristic of a pressure versus time signal characterizing a flow in said first blood line.

11. A blood treatment apparatus, comprising:
a blood treatment component configured to pump blood from an arterial blood line to a venous blood line;
a leak sensor configured to detect a suspected leak with a probability of less than unity in the venous blood line and output a first signal indicating the suspected leak;
an air detector configured to detect infiltration of air into said venous blood line;
a blood flow reversing device controlled by a controller; and
the controller, wherein
the controller is configured to
receive the first signal from said leak sensor, and
to reverse flow responsively to the first signal from said leak sensor such that air infiltrating said venous blood line is detected by said air detector to thereby verify the suspected leak as an actual leak.

12. The apparatus of claim 11, wherein the leak sensor includes a pressure sensor configured to detect pressure changes in said venous blood line.

13. The apparatus of claim 11, wherein the leak sensor includes a data store configured to record a time series of pressure samples representing pressure in said venous blood line and a processor configured to determine a magnitude of a change in pressure within a predefined time interval.

14. The apparatus of claim 11, wherein the leak sensor includes a data store configured to record a time series of pressure samples representing pressure in said venous blood line and a processor configured to determine a magnitude of a change in pressure within a predefined time interval and to indicate a leak when a rate of change in pressure exceeds a predefined range.

* * * * *